(12) United States Patent
Marton et al.

(10) Patent No.: US 7,254,487 B2
(45) Date of Patent: Aug. 7, 2007

(54) METHODS FOR DETERMINING THERAPEUTIC INDEX FROM GENE EXPRESSION PROFILES

(75) Inventors: Matthew Marton, Seattle, WA (US); Roland Stoughton, San Diego, CA (US)

(73) Assignee: Rosetta Inpharmatics LLC, Seattle, WA (US)

( * ) Notice: Subject to any disclaimer, the term of this patent is extended or adjusted under 35 U.S.C. 154(b) by 435 days.

(21) Appl. No.: 09/823,322

(22) Filed: Apr. 2, 2001

(65) Prior Publication Data

US 2001/0012983 A1      Aug. 9, 2001

Related U.S. Application Data

(62) Division of application No. 09/222,582, filed on Dec. 28, 1998, now Pat. No. 6,222,093.

(51) Int. Cl.
   *G01N 33/48*   (2006.01)
   *G01N 31/00*   (2006.01)
   *A01N 37/18*   (2006.01)
   *A01N 43/04*   (2006.01)
   *C12Q 1/00*    (2006.01)
   *C12Q 1/68*    (2006.01)
   *C12Q 1/70*    (2006.01)
   *C12P 21/06*   (2006.01)

(52) U.S. Cl. ............ 702/19; 435/4; 435/6; 435/69.1; 514/2; 514/44; 702/20

(58) Field of Classification Search ............ 435/6, 435/69.1; 702/19
   See application file for complete search history.

(56) References Cited

U.S. PATENT DOCUMENTS

| | | | |
|---|---|---|---|
| 4,946,778 A | 8/1990 | Ladner et al. | 435/69.6 |
| 5,137,877 A | 8/1992 | Kaneko et al. | 514/25 |
| 5,258,453 A | 11/1993 | Kopecek et al. | 525/54.1 |
| 5,332,567 A * | 7/1994 | Goldenberg | 424/1.49 |
| 5,445,934 A | 8/1995 | Fodor et al. | 435/6 |
| 5,510,270 A | 4/1996 | Fodor et al. | 436/518 |
| 5,539,083 A | 7/1996 | Cook et al. | 530/333 |
| 5,556,752 A | 9/1996 | Lockhart et al. | 435/6 |
| 5,569,588 A | 10/1996 | Ashby et al. | 435/6 |
| 5,578,832 A | 11/1996 | Trulson et al. | 250/458.1 |
| 5,645,988 A | 7/1997 | Vande Woude et al. | 435/6 |
| 5,744,305 A | 4/1998 | Fodor et al. | 435/6 |
| 5,777,888 A | 7/1998 | Rine et al. | 364/496 |
| 5,800,992 A | 9/1998 | Fodor et al. | 435/6 |
| 5,811,231 A | 9/1998 | Farr et al. | 435/6 |
| 5,965,352 A | 10/1999 | Stoughton et al. | 435/4 |
| 6,132,969 A | 10/2000 | Stoughton et al. | 435/6 |
| 6,165,709 A | 12/2000 | Friend et al. | 435/4 |
| 6,203,987 B1 | 3/2001 | Friend et al. | 435/6 |
| 6,222,093 B1 | 4/2001 | Marton et al. | 800/3 |
| 6,370,478 B1 | 4/2002 | Stoughton et al. | 435/6 |

FOREIGN PATENT DOCUMENTS

| | | |
|---|---|---|
| EP | 0 534 858 A1 | 9/1992 |
| EP | 0816 511 A1 | 1/1996 |
| WO | WO 88/09810 | 12/1988 |
| WO | WO 90/11364 | 10/1990 |
| WO | WO 94/17208 | 8/1994 |
| WO | WO 97/10365 | 3/1997 |
| WO | WO 97/27317 | 7/1997 |
| WO | WO 98/06874 | 2/1998 |

OTHER PUBLICATIONS

U.S. Appl. No. 60/090,046, filed Jun. 19, 1998, Friend and Stoughton.
U.S. Appl. No. 60/090,004, filed Jun. 19, 1998, Friend and Stoughton.
U.S. Appl. No. 60/084,742, filed May 8, 1998, Friend and Stoughton.
U.S. Appl. No. 60/056,109, filed Aug. 20, 1997, Friend and Hartwell.
U.S. Appl. No. 60/039,134, filed Feb. 28, 1997, Friend and Hartwell.
Alberts, DS et al., 1976 "Rubidazone vs adriamycin: an evaluation of their differential toxicity in the spleen colony assay system", *British Journal of Cancer*, 34: 64-8.
Blanchard et al., 1996, "Sequence to array: Probing the genome's secrets," *Nature Biotechnology* 14:1649.
Blanchard et al., 1996, "High-density oligonucleotide arrays," *Biosensors & Bioelectronics* 11:687-690.
Bryant et al., (1998), "Gene Expression and Genetic Networks," *Pacific Symposium on Biocomputing* 3:3-5. Available Web Site: http://www-smi.stanford.edu/projects/helix/psb98/ Accessed on: Nov. 24, 1998 3:48 p.m.
Bulmer MG, *Principles of Statistics*, M.I.T. Press, Cambridge, Massachusetts, 1967. pp. 117, 221-224.
Carr et al., 1997, "Templates for Looking at Gene Expression Clustering," *Statistical Computing & Statistical Graphics Newsletter* pp. 20-29.

(Continued)

Primary Examiner—John S. Brusca
Assistant Examiner—Eric S. DeJong
(74) Attorney, Agent, or Firm—Jones Day

(57) ABSTRACT

This invention provides methods for determining drug specificity, therapeutic index and effective doses for individual patients. According to the methods of the invention, graded levels of drug are applied to a biological sample or a patient. A plurality of cellular constituents are measured to determine the activity of the drug on a target pathway and at least one off-target pathway. A drug specificity is determined by comparing the target and off target activities of the drug. A therapeutic concentration (or dose) is defined as a concentration (or dose) of the drug that induces certain response in the target pathway. A toxic concentration (or dose) is defined as a concentration (or dose) of the drug that induces certain response in the off target pathway. Therapeutic index is the ratio of the toxic concentration over therapeutic concentration. Methods are also provided to determine an effective dose of a drug for a patient by measuring the activity of the drug on the particular patient.

35 Claims, 11 Drawing Sheets

OTHER PUBLICATIONS

Chee et al., 1996, "Accessing genetic information with high-density DNA arrays," *Science* 274:610-614.

DeRisi et al., 1996, "Use of a cDNA microarray to analyze gene expression patterns in human cancer," *Nature Genetics* 14:457-460.

DeRisi et al., 1997, "Exploring the Metabolic and Genetic Control of Gene Expression on a Genomic Scale," *Science* 278:680-686.

D'haeseleer et al., (1998), "Mining the Gene Expression Matrix: Inferring Gene Relationships From Large Scale Gene Expression Data" Available Web Site: www.cs.unm.edu/~patrik/networks/IPCAT/ipcat.html Accessed on: Nov. 18, 1998 6:16 p.m.

"Experts gather to discuss technologies being developed for functional genomic analysis," *Genetic Engineering News* vol. 16, Nov. 15, 1996.

Fingl E and Woodbury DM, 1975, "Chapter 1: General Principles" *In: The Pharmacological Basis of Therapeutics*, Ch. 1, p. 1.

Fodor et al., 1991, "Light-directed spatially addressable parallel chemical synthesis," *Science* 251:767-773.

Fuhrman et al., (1997), "Genetic Network Inference," *Proceedings of the International Conference on Complex Systems*, Nashua, NH, 21-26. Available Web Site: http://rsb.info.nih.gov/mol-physiol/ICCS/inference/ICCS.html. Accessed on: Nov. 18, 1998 6:14 p.m.

Goffeau et al., 1996, "Life with 6000 genes," *Science* 274:546-567.

Herskowitz, 1987, "Functional inactivation of genes by dominant negative mutations," *Nature* 329:219-222.

Lennon and Lehrach, 1991, "Hybridization analyses of arrayed cDNA libraries" *Trends Genet.* 7:314-317.

Lockhart et al., 1996, Expression monitoring by hybridization to high-density oligonucleotide arrays, *Nature Biotechnology* 14:1675-1680.

Marnellos et al., (1998) "A Gene Network Approach to Modeling Early Neurogenesis in Drosophila," *Pacific Symposium on Biocomputing* 3:30-41. Available Web Site: http://www-smi.stanford.edu/projects/helix/psb98/Accessed on: Nov. 24, 1998 3:48 p.m.

Marton et al., 1998 "drug target validation and identification of secondary drug target effects using DNA microarrays", *Nature Medicine*, 4: 1293-1301.

Michaels et al., (1998), "Cluster Analysis and Data Visualization of Large-Scale Gene Expression Data," *Pacific Symposium on Biocomputing* 3:42-53. Available Web Site: http://www-smi.stanford.edu/projects/helix/psb98/ Accessed on: Nov. 24, 1998 3:48 p.m.

Nguyen et al., 1995, "Differential gene expression in the murine thymus assayed by quantitative hybridization of arrayed cDNA clones," *Genomics* 29:207-216.

Stormo et al., 1998 "drug target validation and identification of secondary drug target effects using DNA microarrays", *Nature Medicine*, 4: 1293-1301.

Thomas et al., 1995, "Dynamical behavior of biological regulatory networks—I. Biological role of feedback loops and practical use of the concept of the loop-characteristic state," *Bull. Math. Biol.* 57:247-276.

van der Krol et al., 1988 "Modulation of Eukaryotic Gene Expression by Complementary RNA or DNA Sequences," *Biotechniques*, 6: 958-676.

Weinstein, JN et al., 1997 "An information-intensive approach to the molecular pharmacology of cancer", *Science*, 275: 343-349.

Wen et al., (1998), "Large-Scale Temporal Gene Expression Mapping of Central Nervous System Development," *Proc. Natl. Acad. Sci. USA* 95:334-339.

Yatscoff, R.W. et al., 1996, "Pharmacodynamic Monitoring of Immunosuppressive Drugs," *Transplantation Proceedings* 28:3013-3015.

Zhao et al., 1995, "High-density cDNA filer analysis: a novel approach for large-scale, quantitative analysis of gene expression," *Gene* 156:207-213.

Stewart, 1998, "Yeast arrays join the search for specific drugs" Molecular Medicine Today 4:48.

\* cited by examiner

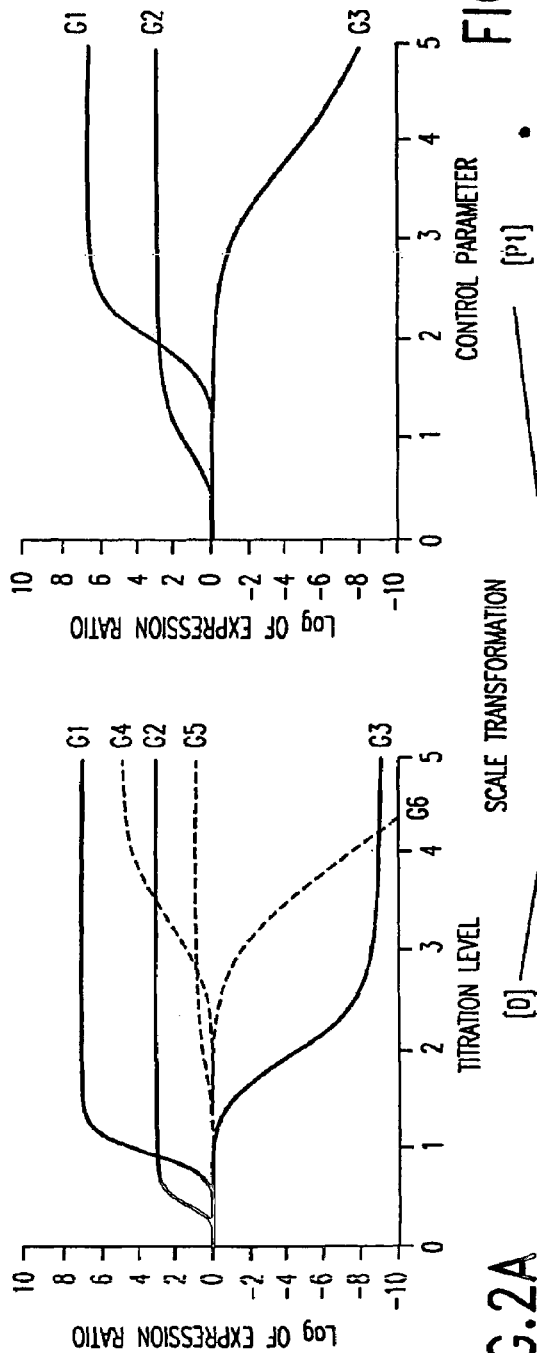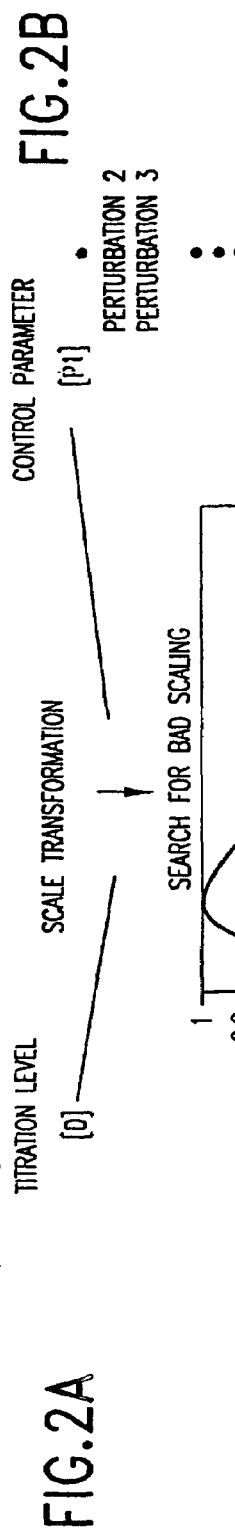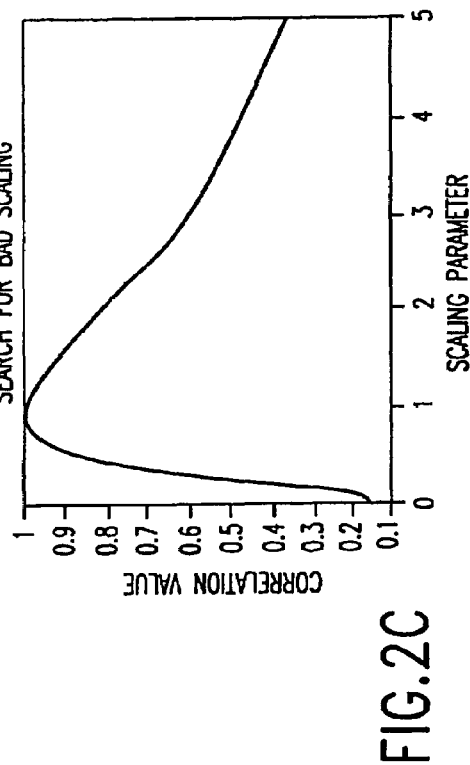
FIG. 2A
FIG. 2B
FIG. 2C

METHODS FOR DETERMINING THERAPEUTIC INDEX FROM GENE EXPRESSION PROFILES

This application is a division of U.S. patent application Ser. No. 09/222,582, filed Dec. 28, 1998, now U.S. Pat. No. 6,222,093, which is incorporated herein by reference in its entirety.

1. INTRODUCTION

The field of this invention relates to methods for assessing or determining the relative therapeutic efficacy versus toxicity of a drug. Specifically, this invention provides methods for evaluating the efficacy and toxicity of a drug by examining the effect of the drug on a target gene expression pathway versus that on off target gene expression pathways. In addition, this invention also provides methods for pharmacodynamic monitoring of drug therapy in individual subjects.

2. BACKGROUND OF INVENTION

The goal of drug discovery is to develop a safe and effective drug. However, most drugs cause adverse reactions in patients. Nies and Spielberg, 1996, Principles of Therapeutics, in THE PHARMACOLOGICAL BASIS OF THERAPEUTICS, (Hardman and Limbird, eds.), McGraw-Hill: New York. The benefits of a drug, therefore, must be evaluated based upon the anticipated benefits and potential adverse reactions. Id. The current methods for assessing safety and efficacy, however, are insufficient to meet the demand of ever increasing speed of drug discovery and individual drug therapy decision making.

2.1. PHARMACOLOGICAL INDICATORS

Various pharmacological indicators have been developed to evaluate drug efficacy and toxicity. Both potency and toxicity of a drug can be evaluated using dose response curves. A dose response curve is a graphic representation of the relationship of dose of a drug applied to a subject versus the response of a subject to the drug (beneficial or toxic effect). Many pharmacological indicators are based upon dose response curves.

Two distinct types of dose response curves are used for estimating various pharmacological indicators. A "graded response curve" depicts a response of an individual subject to varying doses of a drug. A continuously increasing response up to a maximum can be achieved as doses of a drug are increased. A graded response curve is typically a hyperbolic curve. If the dose is in a logarithmical scale, a graded response curve is generally a S-shaped curve. Graded response curves are generally for analyzing individual responses.

A quantal dose response curve is a graphic representation of cumulative frequency of number of subjects responding versus the dose in logarithmic scale. Several important pharmacological indicators are calculated according to the distribution of responding subjects, i.e., the quantal response curve. Medium effective dose ($ED_{50}$) is the dose at which 50% of the population expresses a specified response. Medium lethal dose ($LD_{50}$) is the dose at which 50% of the population dies. Medium toxic dose ($TD_{50}$) is the dose at which 50% of the population expresses a specified toxic effect.

One particularly useful pharmacological indicator is the therapeutic index which is traditionally defined as the ratio of $LD_{50}$ to $ED_{50}$ or the ratio of $TD_{50}$ to $ED_{50}$. Therapeutic index provides a simple and useful indicator of the benefit versus adverse effect of a drug. Those drugs which have a high therapeutic index have a large therapeutic window, i.e., the drugs may be administered over a wider range of effective doses without incurring significant adverse events. Conversely, drugs having a small therapeutic index have a small therapeutic window (small range of effective doses without incurring significant adverse events). Treatment with a drug having a small therapeutic window requires close monitoring.

However, pharmacological indicators, such as the therapeutic index defined above, are often impractical for several reasons. First, as discussed above, those pharmacological indicators are generally determined from the effect of a drug or drug candidate on a population (from quantal response curves), a determination of the above described therapeutic index requires extensive animal or clinical experiments. Such experimentation can be lengthy and costly. Secondly, in vitro experiments, particularly clinical trials, are often conducted at the late stage of drug development. Because of the late stage evaluation, a great expense could incur in researching a drug candidate only to find that the drug candidate has a very low therapeutic index (small therapeutic window).

Therefore, it would be a significant benefit to be able to evaluate the safety and efficacy of a drug candidate during early stages of lead compound selection in drug discovery. Accordingly, this invention provides methods for evaluating drug safety and efficacy that are suitable for early screening of drug candidates.

2.2. DRUG EFFECT IN INDIVIDUALS

Pharmacological indicators, such as the therapeutic index defined above, are only pertinent to a population. The efficacy and toxicity of a drug to an individual, however, may vary due to a number of factors such as genetic variations, and changing physiological or pathological conditions. A "safe" and "effective" drug to a population with a low therapeutic index may become deadly to an individual. Conversely, a drug with a low therapeutic index may be highly effective with tolerable side effects in some individuals.

In a clinical setting, a physician must select, among several drugs, the most effective and safe drug for the patient. In making this decision, the physician needs to know how an particular patient may respond to a drug. One approach to individualized therapy decision making is through pharmacogenetics which relates individual variation in drug response to genetic variations. Pharmacogenetics promises a better understanding of the relationship between genetic variation and drug responses. However, so far, it has only provided limited information related to about 50-100 known drug metabolizing genes. In addition, pharmacogenetics does not address a patients' physiological or pathological conditions.

The second approach is to monitor the clinical symptoms of a patient under drug therapy. This approach is not very effective because signs of toxicity and other effects are often difficult to recognize. See, Yatscoff, et al., 1996, Pharmacodynamic Monitoring of Immunosuppressive Drugs. TRANSPLANT. PROC., 28:3013-3015.

The third approach is to assess the pharmacokinetics, i.e., drug distribution of individual patients. The problem of this approach is that drug concentration may not correlate well with drug effects.

More recently, pharmacodynamic monitoring, which involves the measurement of biological effect of a drug, has been applied to the monitoring of individual patients under drug therapy. In one such clinical experiment, adult bone marrow transplant patients were treated with cyclosporine A (CyA). Pai et al., 1994, Blood 82:3974. The activity of calcineurin (CN), a serine-thronine phosphatase that has an essential role in calcium-dependent signal transduction, was monitored in those patients as an indicator of drug action. The activity of CN, however, was found not to be highly correlated with the effect of the drug. Another problem of the current pharmacodynamic monitoring approach is that only one or few enzymes are monitored. Drug actions, however, are often extensive, directly or indirectly affecting many different pathways.

Therefore, there is a great need for methods useful for monitoring drug actions in individual patients. Accordingly, this invention provides methods useful for monitoring both the beneficial and the toxic effects of a therapeutic regimen during treatment, e.g., to determine optimum doses for a patient which are both safe and effective to that patient.

Discussion or citation of a reference herein shall not be construed as an admission that such reference is prior art to the present invention.

3. SUMMARY OF THE INVENTION

This invention provides methods for evaluating drug efficacy and toxicity. These methods are particularly suitable for evaluation of drug candidates in the early phases of drug discovery. The methods of the invention are also useful for determining the most suitable doses for a particular patient (an animal or a human).

This invention is partially based upon the ability to detect specific actions of a drug on biological pathways. A target pathway of a drug or therapy refers to the biological pathway associated with a particular effect of a therapy, i.e., with a particular "therapeutic effect". An off-target pathway refers to a pathway that is not associated with the particular therapeutic effect. Therapeutic activity of a drug is, therefore, the ability of a drug to affect the target pathway. A drug's activity on off-target pathways represents the nonspecific action of the drug and are not desired. Toxicity or other adverse reaction may result from the nonspecific action on off-target pathways.

Accordingly, this invention provides methods to decompose and compare the drug activity on target and on off-target pathways.

In one aspect of the invention, methods for determining a specificity index of a drug against a target pathway in a biological sample are provided. In some embodiments, the activity of a drug against its target pathway is determined to obtain a target activity ($D_{target}$). The activity of the drug against at least one pathway other than the target pathway is also determined to obtain at least one off-target activity ($D_{off\text{-}target}$). The therapeutic index is calculated according to the formula: $SI = n \cdot D_{target}/\Sigma D_{off\text{-}target}$ where the n is the number of off target pathways.

In some other embodiments, methods of determining a therapeutic index of a drug in a biological sample are provided. In some embodiments, a plurality of levels of the drug is applied to the biological sample. A minimum concentration ($C_{target}$) for inducing a threshold response in a target pathway is determined. A minimum concentration ($C_{off\text{-}target}$) for inducing a threshold response in an off-target pathway is also determined. A therapeutic index is calculated according to the formula: $TI = C_{off\text{-}target}/C_{target}$.

In a particularly preferred embodiment, a drug is applied to a biological sample at graded levels. The responses of a plurality of genes in a target pathway and in off-target pathways are determined. The concentration above which the majority of the genes in the target pathway is induced or repressed by 2 fold, preferably more than 3 fold, more preferably more than 10 fold, is defined as the therapeutic concentration ($C_{target}$). Similarly, the concentration above which the majority of the genes in the off-target pathway is induced or repressed by 2 fold, preferably more than, 3 fold, more preferably more than 10 fold, is defined as the toxic concentration ($C_{off\text{-}target}$).

In yet another aspect of the invention, methods are provided to monitor drug therapy in individual patients. The effect of drug therapy upon a plurality of cellular constituents is measured. The response of cellular constituents is used to decipher the effect of the drug therapy upon target and off-target pathways. Successful therapy scheme should be the one that beneficially affects the target pathway without adversely affecting off-target pathways.

In another aspect of the invention, methods are provided to determine an optimal therapeutic dose of a drug in an individual patient. In some embodiments, a patient is subjected to non-toxic levels of a plurality of perturbations to obtain a perturbation profile consisting of a plurality of cellular constituent measurements. The patient is then subject to a plurality of levels of the drug to obtain a drug response profile consisting of a plurality of cellular constituent measurements. The drug activity on target pathway and off target pathways are determined by decomposing the drug response profile using the perturbation profile.

This invention also provides computer systems and database systems for decomposing drug activities, determining specificity index, calculating therapeutic index, evaluating drug therapies and performing individualized effective dosage determination.

4. BRIEF DESCRIPTION OF THE FIGURES

FIG. 1 illustrates exemplary pathways hypothesized for the action of drug D on a biological system.

FIG. 2A illustrates exemplary responses of expression of genes G1, G2, and G3 in the biological system of FIG. 1 to exposure to drug D (values are normalized to untreated value); FIG. 2B illustrates exemplary responses of genes G1, G2, and G3 in pathway originating at protein P1 to graded perturbations of P1; FIG. 2C illustrates an exemplary correlation between response illustrated in FIGS. 2A-B.

FIG. 3 illustrates response curves of the 30 yeast genes, out of approximately 6000 measured yeast genes, that had the largest expression ratio changes to methotrexate drug exposure; methotrexate exposure levels were 3, 6, 25, 50, 100, and 200 μM; the 100 μM titration resulted in a 50% growth defect; responses have been set to zero at the arbitrary abscissa of −0.5.

Figure 7A:
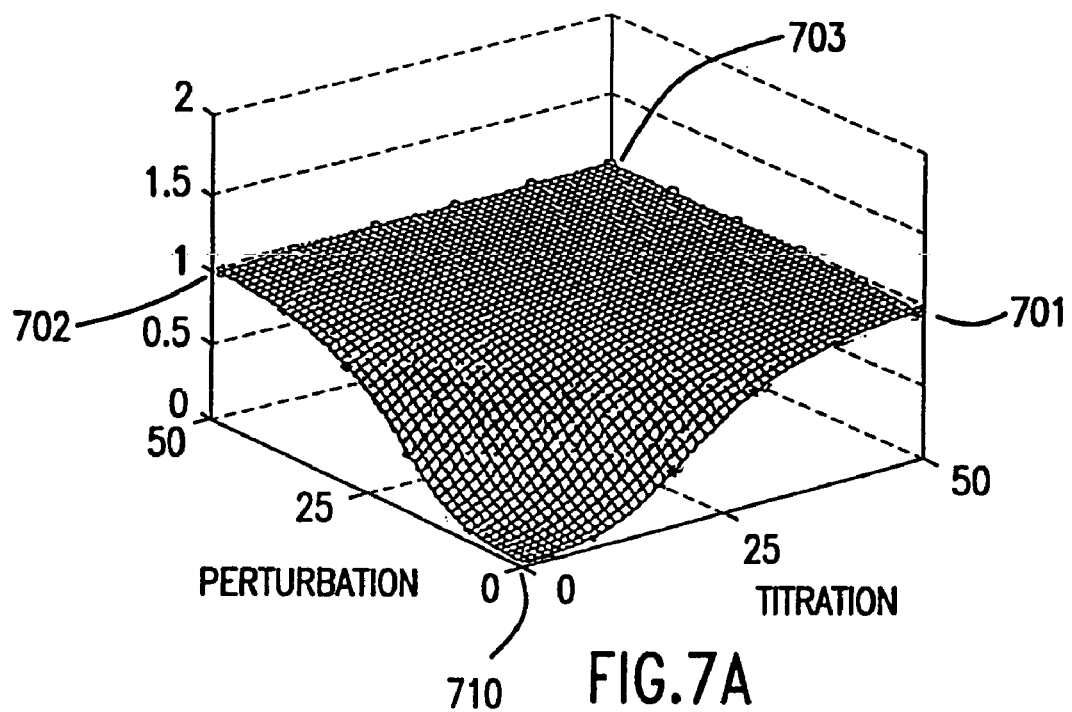
Figure 7B:
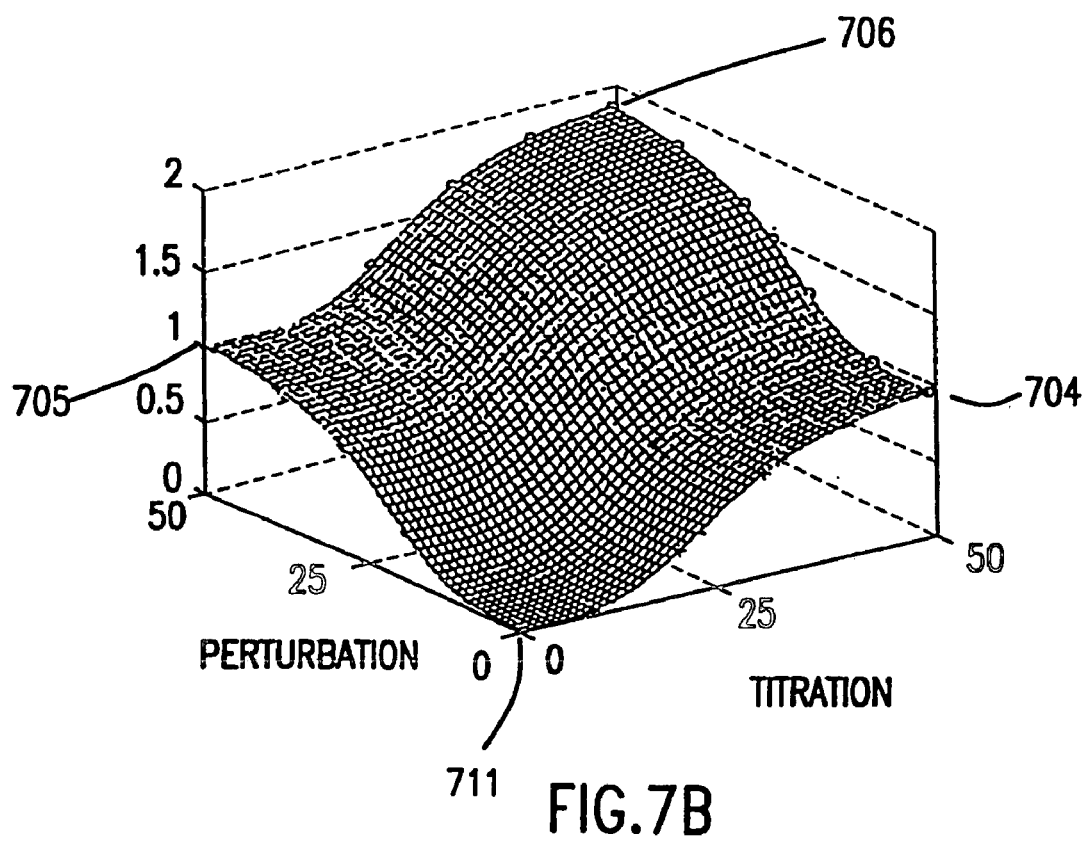

FIGS. 7A-B illustrate surface renderings of Eqns. 10 and 11.

Figure 8A:
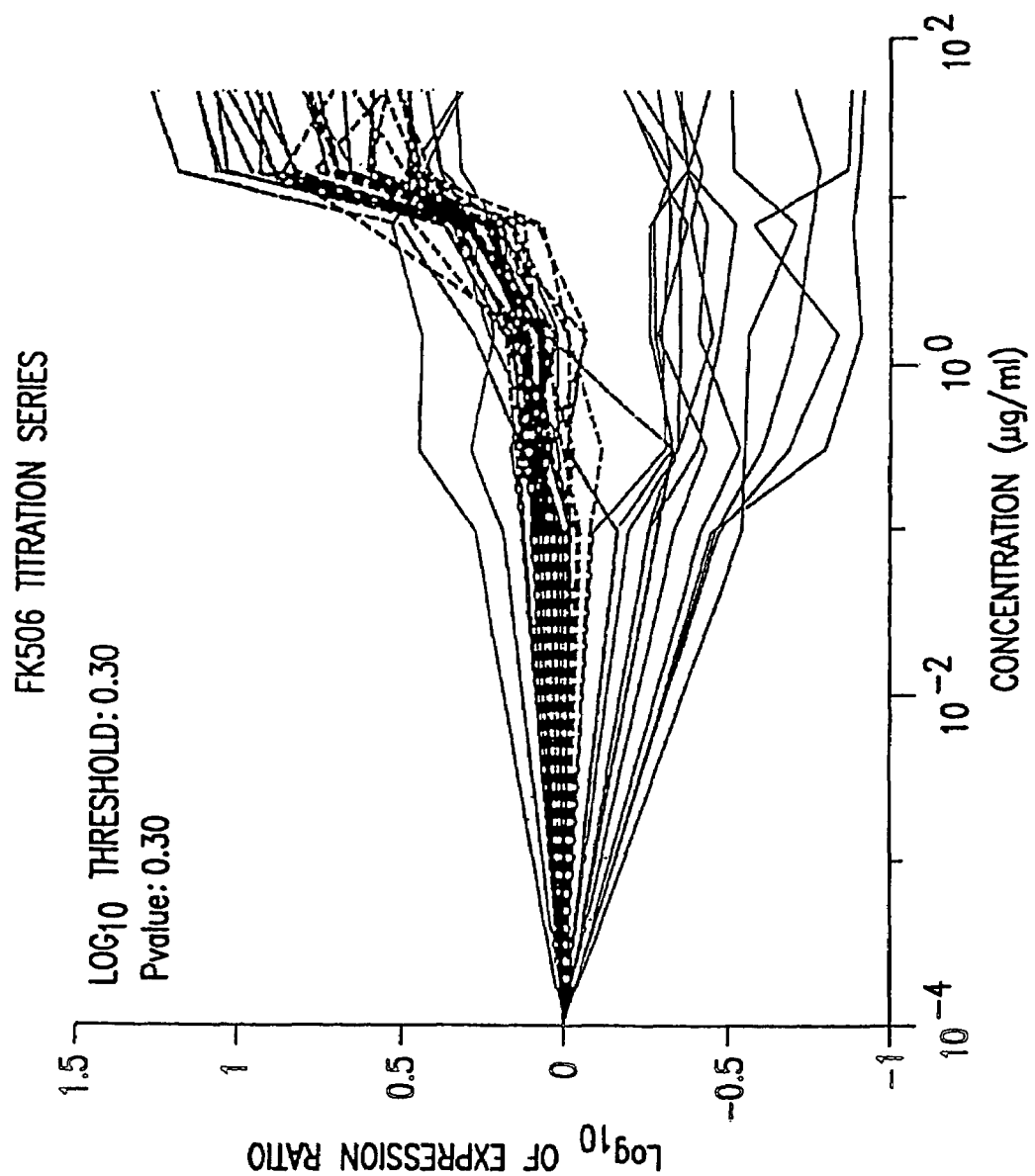
Figure 8B:
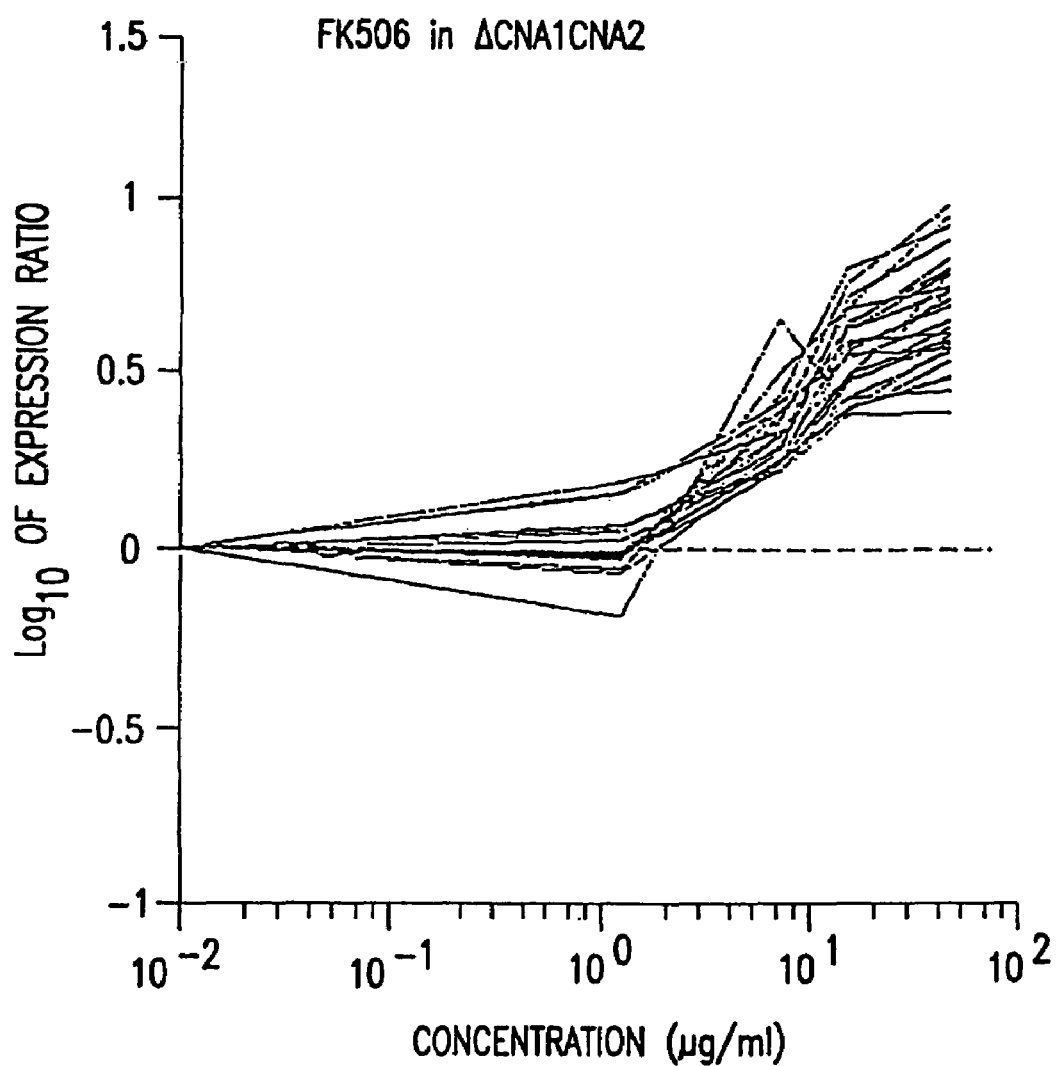
Figure 8C:
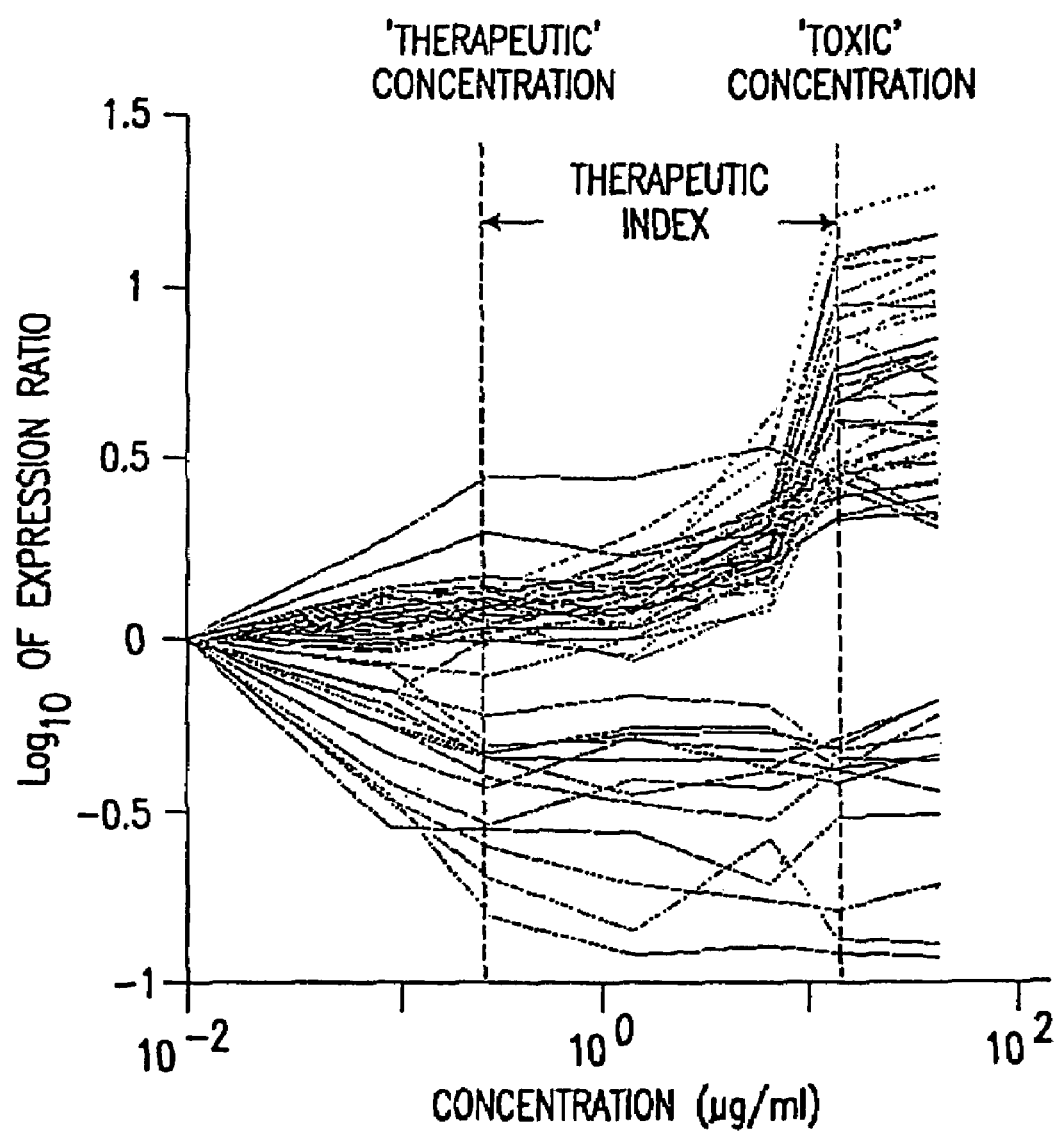

FIGS. 8A-C show the response of a number of yeast genes to FK506.

Figure 9:
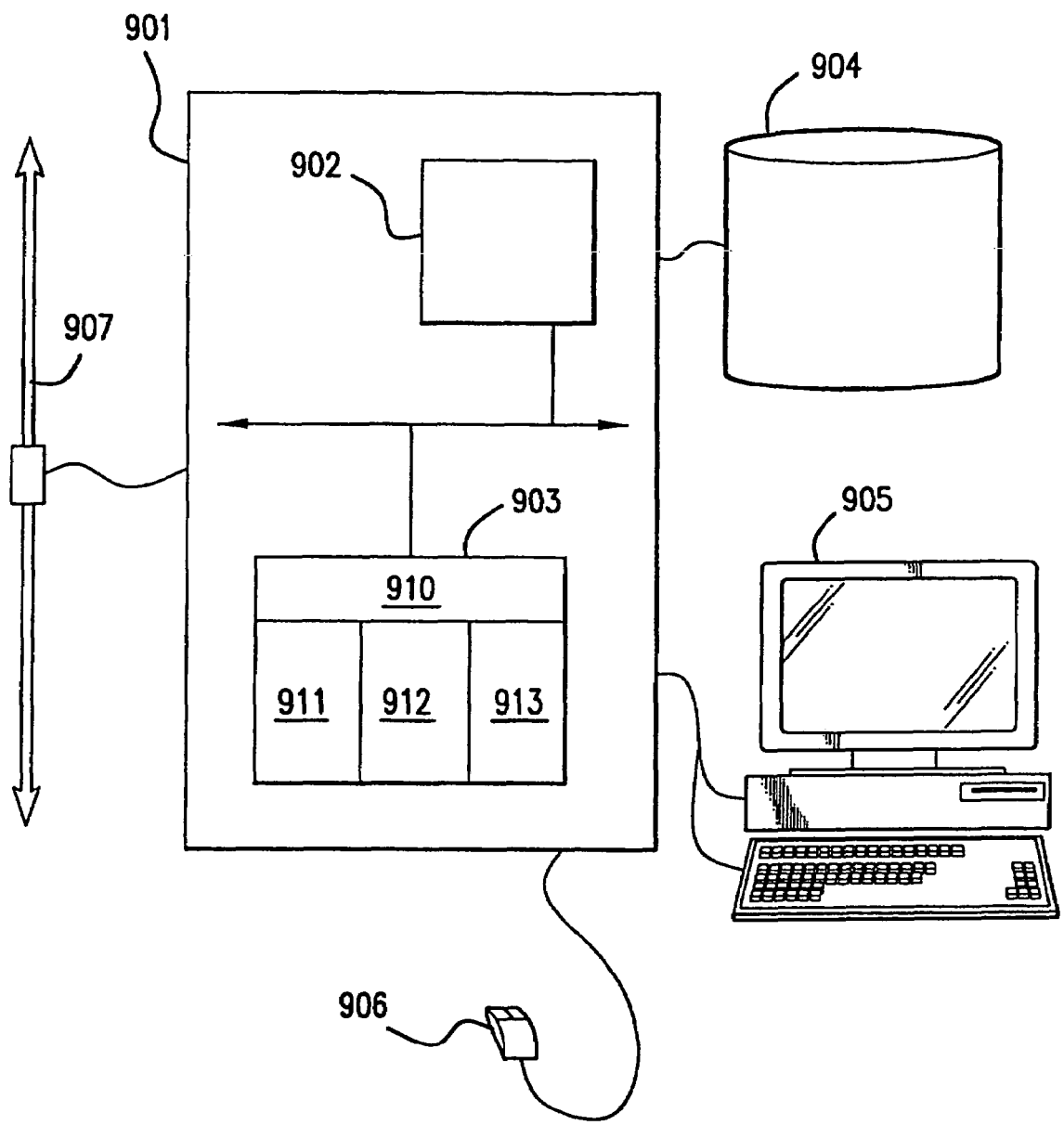

FIG. 9 illustrates an exemplary embodiment of a computer system of this invention.

5. DETAILED DESCRIPTION OF THE INVENTION

This section presents a detailed description of the present invention and its applications. This description is by way of several exemplary illustrations, in increasing detail and specificity, of the general methods of this invention. These examples are non-limiting, and related variants that will be apparent to one of skill in the art are intended to be encompassed by the appended claims.

5.1. INTRODUCTION

A drug exerts its action by affecting biological pathways. If a disease is caused by an alteration of a particular pathway, a drug that specifically restores the state of the pathway may be an effective therapeutic agent for the disease. The effect of a drug, however, is not always specific against a target pathway. "Off-target" pathways may also be affected, which may result in side effects or other adverse reactions.

Accordingly, in one aspect of the invention, the specificity of the actions of a drug is determined by comparing the drug's effect on target pathways and "off-target" pathways in an in vitro model system. In another aspect, this invention provides in vitro models for assessing the relative in vitro efficacy and/or toxicity of a drug candidate. In yet another aspect, this invention provides methods for determining the efficacy and toxicity of a drug on individual patients or animals.

This section first presents certain concepts of the invention, including those of drug action or effect, of the biological state of a cell, and of biological pathways. Next, methods for determining the effect of a drug on different pathways are presented. The following sections present methods of the invention.

5.1.1. DRUG ACTION AND BIOLOGICAL PATHWAYS

Drugs, as defined herein, are any compounds of any degree of complexity that perturb a biological system, whether by known or unknown mechanisms, whether or not they are used therapeutically, and whether or not their effects are beneficial (e.g., therapeutic) or toxic to a biological system. Drugs thus include: typical small molecules of research or therapeutic interest; naturally-occurring factors, such as endocrine, paracrine, or autocrine factors or factors interacting with cell receptors of all types; intracellular factors, such as elements of intracellular signaling pathways; factors isolated from other natural sources; and so forth. The biological effect of a drug may be a consequence of, inter alia, drug-mediated changes in the rate of transcription or degradation of one or more species of RNA, the rate or extent of translation or post-translational processing of one or more polypeptides, the rate or extent of the degradation of one or more proteins, the inhibition or stimulation of the action or activity of one or more proteins, and so forth. In fact, most drugs exert their affects by interacting with a protein. Drugs that increase rates or stimulate activities of a protein are called herein "activating drugs," while drugs that decrease rates or inhibit activities of a protein are called herein "inhibiting drugs."

Figure 1:
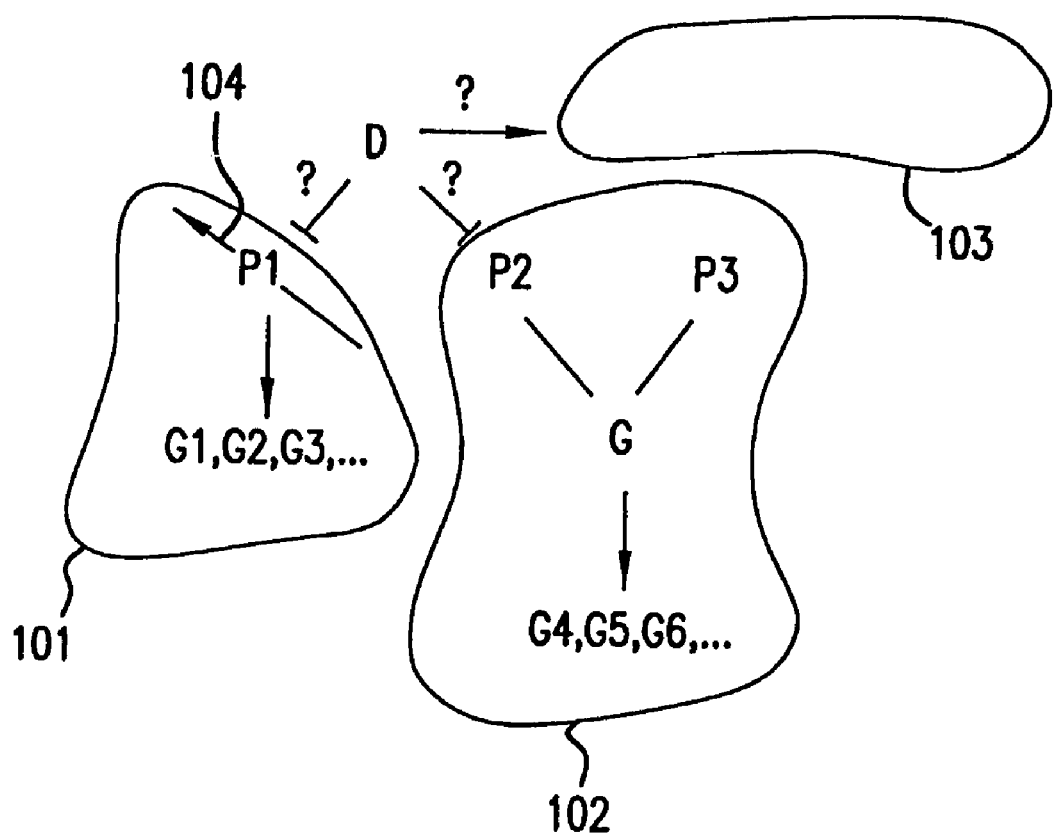

Drug effects on a cell, whether therapeutic or toxic and however measured in a particular implementation, are generally represented by combining the effects of the drug on individual pathways. For example, FIG. 1 illustrates that drug D acts on a cell by interacting with biological pathways 101, 102, and 103 (details of pathway 103 are not illustrated). The arcs between drug D and these pathways represent possible action of drug D on these pathways. The entire action of drug D on the cell is assumed to be expressible as a combination of drug D's actions on one or more of these three pathways. In the following paragraphs, first, biological pathways as generally used according to this invention are described, followed by description of particular biological pathways to which this invention is advantageously applied.

As used herein, a biological pathway is generally understood to be a collection of cellular constituents related in that each cellular constituent of the collection is influenced according to some biological mechanism by one or more other cellular constituents in the collection. The cellular constituents making up a particular pathway can be drawn from any aspect of the biological state of a cell, for example, from the transcriptional state, or the translational state, or the activity state, or mixed aspects of the biological state. Therefore, cellular constituents of a pathway can include mRNA levels, protein abundances, protein activities, degree of protein or nucleic acid modification (e.g., phosphorylation or methylation), combinations of these types of cellular constituents, and so forth. Each cellular constituent of the collection is influenced by at least one other cellular constituent in the collection by some biological mechanism, which need not be specified or even known or understood. In illustrations presented herein, the influence, whether direct or indirect, of one cellular constituent on another is presented as an arc between the two cellular constituents, and the entire pathway is presented as a network of arcs linking the cellular constituents of the pathway. A biological pathway, therefore, refers both to the collection of cellular constituents drawn from some aspect of the biological state together with the network of influence between the constituents.

For example, in FIG. 1, biological pathway 101 includes protein P1 (for example, either the abundance or activity of P1) and genes G1, G2, and G3 (for example, their transcribed mRNA levels) together with the influence, direct or indirect, of protein P1 on these three genes, represented as the arc leading from P1 to these three genes. The mechanism of this influence might arise, for example, because protein P1 can bind to promoters of these genes and increase the abundances of their transcripts.

In summary, therefore, as used herein, a biological pathway includes a collection of cellular constituents that influence one another through any biological mechanism, known or unknown, such as by a cell's synthetic, regulatory, homeostatic, or control networks. The influence of one cellular constituent on another can be, inter alia, by a synthetic transformation of the one cellular constituent into the other, by a direct physical interaction of the two cellular constituents, by an indirect interaction of the two cellular constituents mediated through intermediate biological events, or by other mechanisms.

5.1.2. EXEMPLARY BIOLOGICAL PATHWAYS

Concrete examples of biological pathways, as understood herein, are well known in the art. They depend on various biological mechanisms by which the cellular constituents influence one another. Biological pathways include well-known biochemical pathways, for example, pathways for protein and nucleic acid synthesis. The cellular constituents of synthetic pathways include enzymes and the synthetic intermediates, and the influence of a precursor molecule on a successor molecule is by direct enzyme-mediated conversion. Biological pathways also include signaling and control pathways, many examples of which are also well known. Cellular constituents of these pathways include, typically, primary or intermediate signaling molecules, as well as the proteins participating in the signal or control cascades usually characterizing these pathways. In signaling pathways, binding of a signal molecule to a receptor usually directly influences the abundances of intermediate signaling molecules and indirectly influences the degree of phosphoylation (or other modification) of pathway proteins. Both of these effects in turn influence activities of cellular proteins that are key effectors of the cellular processes initiated by the signal, for example, by affecting the transcriptional state of the cell. Control pathways, such as those controlling the timing and occurrence of the cell cycle, are similar. Here, multiple, often ongoing, cellular events are temporally coordinated, often with feedback control, to achieve a consistent outcome, such as cell division with chromosome segregation. This coordination is a consequence of functioning of the pathway, often mediated by mutual influences of proteins on each other's degree of phosphorylation (or other modification). Also, well known control pathways seek to maintain optimal levels of cellular metabolites in the face of a fluctuating environment. Further examples of cellular pathways operating according to understood mechanisms will be known to those of skill in the art.

As noted above, the present invention is directed to determining the relative toxicity of drugs, and, in particular, to distinguishing between therapeutic and toxic pathways of drug action. Certain types of biological pathways are therefore of particular interest. Drugs typically act on a cell by directly interacting with one cellular constituent, and, more usually, with a plurality, e.g., of 5 to 10, to 50, or more cellular constituents. Therefore, pathways of particular interest in this invention include those that originate at particular cellular constituents, and, especially, are hierarchical.

A pathway originating at particular cellular constituents includes, as a first group, those particular cellular constituents, a second group of cellular constituents constituents that are directly influenced by the first group of cellular constituents (i.e., the particular cellular constituents), a third group of cellular constituents that are directly influenced by the second group of cellular constituents, and so forth, along with the network of influences between the groups of cellular constituents. Influences between the cellular constituents can be according to any biological mechanism, for example, a signaling mechanism, or a regulatory or homeostatic control mechanism, or a synthetic mechanism. In FIG. 1, pathway 101, including a protein and several genes, originates at protein P1. Pathway 102, including two proteins and several genes, originates at proteins P2 and P3.

Biological pathways can also be either hierarchical or non-hierarchical, with hierarchical pathways being of particular interest in this invention. Generally, a hierarchical biological pathway has no feedback loops. In more detail, a hierarchical pathway is one in which its cellular constituents can be arranged into a hierarchy of numbered levels so that cellular constituents belonging to a particular numbered level can be influenced only by cellular constituents belonging to levels of lower numbers. A hierarchical pathway originates from the lowest numbered cellular constituents. In FIG. 1, pathways 101 and 102 are hierarchical. Pathway 101 is clearly hierarchical. In pathway 102, proteins P2 and P3, on a lowest numbered level, both directly affect gene G, on an intermediate numbered level. In turn, gene G, perhaps indirectly, affects genes G4, G5, and G6, all on a highest numbered level. In contrast, a non-hierarchical pathway has one or more feedback loops. A feedback loop in a biological pathway is a subset of cellular constituents of the pathway, each constituent of the feedback loop influences and also is influenced by other constituents of the feedback loop. For example, in pathway 102 of FIG. 1, if gene G6, either directly or indirectly, affected protein P3, a feedback loop including genes G and G6 and protein P3 would be created.

When describing biological pathways associated with drug response, those cellular constituents which interact directly with a drug are called herein the "targets" of the drug. Further, effects of the drug on the cell flow from other cellular constituents influenced, directly or indirectly, by the direct targets of the drug. Accordingly, the originating cellular constituents of the pathways of interest in this invention are preferably those that are potential drug targets. Since most drug targets are proteins, pathways originating at cellular proteins are of particular interest in this invention. Hierarchical pathways are also of interest in representing drug action, including drug toxicity, because the feedback loops present in non-hierarchical pathways can obscure drug effects by causing compensating influences in cellular constituents that mute drug influences.

Although drugs will usually interact directly with a plurality of cellular constituents, more typically with a plurality of proteins, usually only direct interactions with a relatively small number of these cellular constituents are associated with any specific, desired, therapeutic biological effect of the drug. Most preferably, only the direct interaction of the drug with one particular cellular constituent, preferably with a particular protein, is associated with a specific, desired, therapeutic effect. The specific, desired, therapeutic biological effect of a drug is referred to herein as the "therapeutic effect" of the drug. Accordingly, the particular cellular constituent (or less preferably, constituents) which interact(s) directly with a drug and is (are) associated with the therapeutic effect of a drug is (are) referred to herein as the drug's "primary target(s)".

The other cellular constituents which interact directly with the drug but which are not primary targets of the drug are generally associated with other effects of the drug which are not desired and do not have a therapeutic benefit to the subject, e.g., they may be lethal or toxic. Such effects are referred to herein as "toxic effects". Specifically, a "toxic effect" of a drug, as used herein, is any effect which is not a therapeutic effect. Those cellular constituents which interact directly with a drug and are associated with toxic effects are referred to herein as "off-targets" of the drug.

The following descriptions of the various embodiments of this invention, for economy of language only and without any limitation, are primarily directed to pathways, and often only to hierarchical pathways, originating at particular proteins. In view of the following description, it will be apparent to one of skill in the art how to apply the invention to pathways, including non-hierarchical pathways, originating at other cellular constituents, such as mRNA abundances.

5.1.3. IDENTIFICATION OF BIOLOGICAL PATHWAYS

The method of the invention is based upon the decomposition of drug response of individual cellular constituents into the responses of different biological pathways. Identification of biological pathways is often the first step for decomposition of drug responses. However, in some embodiments, the decomposition of biological pathways is simultaneously achieved with the identification of biological pathways.

Biological pathways, particularly pathways involved in drug actions, i.e., pathways that originate at a drug target (e.g., proteins) and/or are hierarchical, can be identified for use in this invention by several means. Such means for identifying such pathways have been described, in detail, by Stoughton and Friend, U.S. application Ser. No. 09/074,983, filed on May 8, 1998, now U.S. Pat. No. 5,965,352, and Stoughton and Friend, U.S. application Ser. No. 09/179,569, filed on Oct. 27, 1998, which are incorporated herein by reference in their entireties.

Biological pathways for use in this invention can be identified in sufficient detail by measurements of aspects of the biological state of a cell, for example, by measurements of the transcriptional state, or of the translational state, or of the activity state, or of mixed aspects of the biological state. By measurements of an aspect of the biological state of a cell subject to various perturbing conditions, such as conditions resulting from exposure to various drugs or from various genetic manipulations, collections of cellular constituents that vary in a correlated fashion can be identified. Correlated variation means herein that the relative variation of the cellular constituents in the collection, in other words the pattern of variation of the cellular constituents, is similar in the different conditions. A network of mutual influences linking the collection of constituents into a biological pathway can be inferred from the similar pattern of variations in different conditions. When the various conditions during measurement act on the biological pathway, the constituents of the pathway respond with similar patterns of variation determined by the type and direction of their mutual influences. Even if neither the exact network of influences nor the mechanism of their action is known, this collection of constituents can be used as one biological pathway in this invention.

For example, a drug known to act at a single defined target can be used to measure the pathway originating from this target. A cell is exposed to varying concentrations of the drug and the cellular constituents of an aspect of the biological state, for example, the transcriptional state, are measured. Those cellular constituents that vary in a correlated pattern as the concentrations of the drug are changed can be identified as a pathway originating at that drug. As previously disclosed, genes with co-varying transcription in response to a wide variety of perturbations can be grouped by cluster analysis into genesets. Each of the genesets may represent a potential biological pathway. See, Stoughton and Friend, U.S. patent application Ser. No. 09/179,569, filed on Oct. 27, 1998, incorporated herein by reference in its entirety for all purposes.

Additionally, as in the case of already known pathways, sub-pathways of a measured pathway can be determined if measurement during exposure to further conditions reveals that sub-collections of the original pathway vary according to different patterns. These differently varying sub-collections then constitute sub-pathways applicable in this invention. Cellular constituents of the measured pathway can be grouped according to the sub-pathway through which they are most affected.

For example, where a pathway has been identified by measurements of a cell exposed to varying concentrations of a drug, sub-pathways can be identified by performing gene knockouts on the cell. By measuring, e.g., the transcriptional state of a cell exposed to the drug and having certain gene knockouts, sub-pathways of the drug pathway originating at the deleted gene can be identified.

Graded pathway perturbations can also be performed in several manners. In the case of known or measured pathways which originate from known proteins or other cellular constituents, the abundance or activity of these proteins or other cellular constituents can be perturbed in a graded manner by methods such as mutation, transfection, controllable promoter systems, or other drugs of specific known action.

5.1.4. DECOMPOSITION OF DRUG RESPONSES INTO PATHWAY CONTRIBUTIONS

The method of invention is based upon the ability to analyze the response of a biological system to the response of pathways. One particularly useful method for decomposing the drug response is by comparing measurements of changes in the biological state of a cell in response to graded drug exposure with measurements of changes in the biological state of biological pathways that are likely to be involved in the effects of the drug, the changes being in response to graded perturbations of these pathways.

Aspects of the biological state of a cell, for example, the transcriptional state, the translational state or the activity state, are measured in response to a plurality of strengths of drug exposure, preferably graded from drug absence to full drug effect. The collection of these measurements, optionally graphically presented, are called herein the "drug response".

In some embodiments, the biological state of a cell can be more advantageously represented by cellular constituent sets. Id. Cellular constituent sets are a groups of covarying cellular constituents. For example, genes with co-varying transcription are grouped into genesets. By a projection process described in detail in U.S. patent application Ser. No. 09/179,569, previously incorporated by reference, cellular constituent values can be converted into cellular constituent set values, e.g., geneset values. The resulting profile of cellular constituent set values have a smaller dimension and a low measurement errors than the original profile of cellular constituents. Throughout this application, in places where cellular constituents are used to represent cellular state or to measure drug pathway activities, cellular constituent set values (e.g., geneset values) may be more advantagously used in the place of cellular constituent sets. For example, drug responses can be represented by the change in cellular constituent set values.

Cellular constituents varying in the drug response are compared to cellular constituents varying in the pathway responses in order to find that biological pathway, or combination of biological pathways, which matches all or substantially all of the drug response. Substantially all of a drug response is matched by pathway responses when most of the cellular constituents varying in the drug response are found to vary in a similar fashion in one or more of the pathway responses. Preferably, at least 75% of the cellular constituents varying in the drug response can be matched, more preferably at least 90% can be so matched, and even more preferably at least 95% can be so matched. Cellular constituents vary in a similar fashion in two responses when both sets of data are likely to be the same in view of experimental error.

In a preferred embodiment, comparison of a drug response with one or more pathway responses is performed by a method in which an objective measure of differences between the measured drug response and a model drug response is minimized. The model drug response is constructed by combining the pathway responses of those pathways considered likely to be involved in the effects of the drug. If a particular cellular constituent varies in only one pathway response, the variation of that cellular constituent in the model drug response is the variation in that one pathway response. If a particular cellular constituent varies in two or more pathway responses, the variation of that cellular constituent in the model drug response is a combination of the variation in the pathway responses. This combination can be performed additively or by another numerical combination.

Since the relation of the strength of the drug (described, for example, by the kinetic constants describing its actions) to the effectiveness of the graded pathway perturbation (described, for example, by arbitrary measures of a perturbation control parameter) is not known, an adjustable scaling is made between the intensity of the graded perturbations for each pathway response that are combined in the model drug response and the graded drug exposures. The variations of the cellular constituents are combined together into the model drug response with adjustable scalings. The adjustable scaling for one pathway is usually independent of the scalings for the other pathways.

In one embodiment, the objective measure can be minimized by adjusting the scaling of each pathway response in the model drug response and/or by varying the number or identity of biological pathways combined in the model drug response. Varying the pathways combined in the model drug response can be simply achieved by setting the adjustable scalings in the biological pathways not desired so that no variation in the cellular constituents occurs. In a preferred embodiment, where the adjustable scalings are performed by linear transformation between the pathway perturbation parameters and the drug exposure, minimization of the objective measure can be performed by standard techniques of numerical analysis. See, e.g., Press et al., 1996, *Numerical Recipes in C,* 2nd Ed. Cambridge Univ. Press, Ch. 10.; Branch et al., 1996, *Matlab Optimization Toolbox User's Guide,* Mathworks (Natick, Mass.). Also, the method of numerically combining variations of the same cellular constituent from different pathways can be varied. For example, multiplicative cross-product terms could be included which would represent, inter alia, multiplicative responses from multiple transcription factors coming together from different convergent pathways to form a transcription complex.

The pathways combined in the model drug response in order to represent measured drug response in advance of minimization of the objective function can be chosen in various ways. Most simply a large collection of biological pathways covering many cellular functions can be combined with independently adjustable scalings; the objective measure minimized; and the combination of biological pathways best representing the drug response determined. A "compendium" of biological pathways is a set of pathways which is substantially complete in the biological system used for the assay, or at least sufficiently complete to cover all pathways likely to be relevant for drug action. Preferably, the minimization is made more efficient if the collection of pathways can be narrowed to those likely to be involved in the action of the drug. Such narrowing can be predicated on, for example, prior knowledge of drug effect and biological pathway significance.

More preferably, pathways are selected that originate at particular cellular constituents, and advantageously, are also hierarchical (minimizing the muting effects of negative feedback loops or the amplifying effects of positive feedback loops). Most preferably, the originating cellular constituents are likely to be targets of the drug of interest, usually functionally active proteins. For example, given a drug of interest and a selection of potential targets in the cell, first, the biological pathways originating at each of the potential targets can be measured (as previously described in Section 5.1). Second, these pathways can be combined with independent scaling factors, the objective measure minimized, and the combination of pathways best representing the drug's action determined. Thereby, along with determination of the actual pathways involved in drug action, the actual targets of the drug are also identified as the cellular constituents from which the actual pathways originate.

After the pathways involved in drug action are determined, they can be confirmed by the following additional methods of this invention. According to a first confirmation method, the significance of the pathways determined is decided based on statistical tests referencing the minimum value computed from the objective measure. One preferred test computes pathway representations as above with a plurality of randomizations of the drug response data in order to determine a distribution of minimum values of the objective measure. The statistical significance of the minimum value of the objective measure actually obtained from the un-randomized drug response data can be judged against this distribution.

According to a second confirmation method, determined pathways can be confirmed by making measurements of a cell simultaneously both exposed to the drug and also having one or more of the determined pathways perturbed. By perturbing drug exposed cells (or applying a drug to perturbed cells), verification can be obtained that the pathway is in fact involved in the response of specific downstream genes and proteins. If the biological pathways perturbed are not involved in the action of the drug, the drug and the perturbations will produce independent, usually substantially additive, effects on the variation of cellular constituents. If the biological pathways perturbed are indeed involved in the action of the drug, the effects of the drug and the perturbations will not be independent. The effects will interfere and the variation of cellular constituents will saturate at values observed for either drug exposure or pathway perturbations alone.

The following paragraphs generally illustrate several of the methods of this invention with respect to FIG. 1 and FIGS. 2A-C. FIG. 1 illustrates drug D that may act on a cell through three potential pathways. Pathways 101 and 102 originate with proteins P1 and P2 and P3, respectively, and ultimately influence the expression levels of the indicated genes, perhaps by influencing additional mediating cellular constituents. The details of pathway 103 are not illustrated. The methods of this invention determine which of these three pathways, alone or in some combination, explains the actual action of drug D on the cell To make this determination, the methods of this invention attempt to represent drug D's action on the cell, that is its drug response, by a combination of the pathway responses of pathways 101, 102, and 103. This representation will be successful, and drug D's response will be adequately represented, for that combination of pathways which drug D actually effects. If the observed response of drug D can be represented adequately by only one of the pathway responses, that pathway is identified as being the only pathway of action for drug D.

In the case of pathways 101 and 102 which originate at proteins P1 and P2 and P3, respectively, the pathway responses can be directly determined by known perturbations of the abundance, or activity, or some other characteristic relevant for drug D's action, of the originating proteins. For example, application of variable perturbation 104 changes a relevant characteristic of protein P1, thereby influencing characteristics of the other cellular constituents in pathway 101, for example, the expression levels of genes G1, G2, and G3. Perturbation 104 is capable of being applied in a graded fashion in order to generate pathway responses at a plurality of perturbation control values, from the native level of the characteristic of protein P1 perturbed to full saturation or inhibition of that characteristic. Similar known perturbations can be made to protein P2 and the expression levels of genes G4, G5, and G6 measured.

Additionally, if the response of drug D on a cell can be represented as pathway responses generated by perturbing P1 or P2, one of skill on the art will appreciate that these P1 or P2 are thereby identified as protein targets of drug D.

FIG. 2A illustrates a possible transcriptional response of a cell to drug D. The horizontal axis indexes the degree of drug exposure, for example, the concentration of the drug in the cell's environment, ranging from no exposure at the value 0 to saturating exposure at the value 5. The vertical axis indexes the logarithm of the ratio of the gene expression on exposure to drug D to the gene expression in the absence of drug D. Accordingly, the drug response curves all begin at 0 in the absence of drug D, corresponding to an expression ratio of 1. It is assumed for the purposes of this example that only genes G1, G2, and G3 of a cell significantly respond to exposure to drug D with the response indicated by the labeled response curves.

Although the gene response curves are presented for the purposes of illustration as continuous curves, in an actual experimentally determined drug response, expression ratios are measured for only a limited set of discrete levels of drug exposure. In an actual case, the graphical representation of a drug response would consist of expression ratios only at these discrete exposure levels. Preferably, the discrete drug exposure levels are chosen and positioned so that the steepest regions of the drug response curves are adequately sampled. Preferably, at least 5 and more preferably 10 or more exposure levels are positioned in these regions of the response curves, where the drug response varies from the unexposed level to the saturating level.

Such response curves can be generated and measured by the methods of Sections 5.5. In particular, by employing technologies for gene expression analysis in concert with the genome sequence of the yeast *S. cerevisiae,* such response curves can be experimentally generated for nearly all of the genes in that yeast. Although much of the description of this invention is directed to measurement and modeling of gene expression data, this invention is equally applicable to measurements of other aspects of the biological state of a cell, such as protein abundances or activities.

FIG. 2B illustrates a possible pathway response for pathway 101 (in FIG. 1), which originates with protein P1 and involves the expression levels of genes G1, G2, and G3, in response to perturbation 104 to originating protein P1. The horizontal axis in this figure indexes the strength of perturbation 104 applied to P1, ranging from no perturbation of P1 at the value 0 to saturating perturbation of P1 at the value 5. Perturbation 104 can be either inhibiting or activating protein P1 as the case may be. As set out in more detail in Section 5.4, such perturbation might be accomplished, inter alia, by transfection with varying amounts of a gene expressing P1 in order to increase the abundance of P1, or by expression of P1 under the control of a controllable promoter in turn controlled by a drug or small molecule, or by inhibition of P1 activity by exposure to a different drug of specific known action against P1. Similarly to FIG. 2A, the vertical axis in FIG. 2B indexes the logarithm of the ratio of the gene expression on exposure to perturbation 104 to the gene expression in the absence of perturbation 104. The response of the expression levels of genes G1, G2, and G3, which are components of pathway 101 influenced by protein P1 (whether directly or indirectly), are illustrated by the labeled curves.

Also similarly to FIG. 2A, although these pathway response curves are illustrated as continuous, in actual fact perturbation 104 to protein P1 would be applied at a limited set of discrete values and the "curves" are actually expression ratio values at these discrete perturbation control parameter values. Also preferably, the discrete perturbation values are chosen and positioned so that the steepest regions of the pathway response curves are adequately sampled, with at least 5 and more preferably 10 or more perturbation control parameter values positioned in the regions of the response curves where the responses vary from the unexposed level to the saturating level.

The drug and pathway response curves in FIGS. 2A and 2B illustrate the generally expected shape of such curves. This expected shape includes a below threshold region at low drug exposure or perturbation control parameter over which there is effectively no response of the cellular constituents in the pathway. After this below threshold region, the drug or perturbation begins to be efficacious and the values of characteristics of the cellular constituents are perturbed. The curve of perturbed values is expected to usually have a monotonic increase or decrease toward an asymptotic level at saturation beyond which no further change is observed. The response curves terminate in this saturation region.

In fact, more complicated, non-monotonic response curve shapes are possible and expected in some situations. For example, in the case where the drug or the perturbation has toxic effects, as toxicity sets in rising abundances of cellular constituents may start to fall and falling abundances may start to fall even faster. Also, nonlinear and feedback mechanisms known to be present in the biological systems may result in non-monotonic, multi-phasic responses. Such a response might first increase and then decrease with increasing perturbation amplitude or drug exposure. For example, a drug or a perturbation may act on certain cellular constituents through two pathways with different thresholds and with opposite effects to generate increasing then decreasing (or vice versa) responses. Although the methods of this invention are illustrated and primarily described with respect to monotonic response curves, such as illustrated FIGS. 2A-B, as will be apparent to one of skill in the art from subsequent description, these methods are equally applicable to non-monotonic response curves.

Having measured drug and pathway responses, the problem of determining the pathways by which drug D (of FIG. 1) acts on a cell requires matching the drug response as a combination of pathway responses. FIG. 2A illustrates how the abundances of genes G1, G2, G3, G4, G5, and G6 vary in the drug response of drug D. Since these same genes vary in the disjoint pathways originating at P1 and P2, it can be determined according to the methods of this invention whether either of these two pathway is actually involved in the response of drug D.

According to the methods of this invention, these determinations are made by inquiring whether the pathway response curves of the pathways originating at P1 and P2 can be transformed to match the drug response curves of FIG. 2A. Concerning only the pathway originating at protein P1, the determination of whether this pathway is actually involved in the action of drug D is met by attempting to transform the pathway response curves of this pathway, illustrated in FIG. 2B, into the drug response curves for G1, G2, and G3, illustrated in FIG. 2A. The drug response curves for G4, G5, and G6 need not be considered here because the pathway originating at P1 does not affect these genes.

The transformation of the pathway response curves of FIG. 2B into the drug response curves of FIG. 2A generally can have both a vertical and a horizontal component. No vertical transformation of these response curves is expected in this example. The amplitudes of both sets of response curves will be the same, since they both vary over the same range, from 0, in a resting state without perturbation or drug exposure, to saturation, in a state where both drug and the perturbation have maximally affected pathway 101. However, horizontal transformation is likely to be necessary. Because there is no reason for the values defining the perturbation control, such as the exposure value of a viral transfection vector expressing P1, or controllable promoter of P1 expression, or another drug of specific known action on P1, to be the same as the values defining exposure to drug D under study, the drug and pathway response curves must be horizontally transformed in order to ascertain any possible match. Since the curves for G1, G2, and G3 in FIG. 2B have the same general shape as the corresponding curves in FIG. 2A, such a horizontally transformation is likely to be possible in this case.

Finding a horizontal transformation, according to this invention, proceeds by parameterization of a class of possible transformations. Then, optimum values of the parameters are sought that will make the pathway response explain the drug response as closely as possible. A preferable and simple class of transformations are linear scaling from values of the perturbation control parameter to values of the drug exposure, which are simply parameterized by the degree of stretch or shrinkage. Optimum values of the linear stretch can then be found by standard means, such as by minimization of an objective measure of the difference of the pathway and drug response curves.

FIG. 2C sets forth an exemplary illustration of finding an optimum linear scaling parameter. The vertical axis of the graph of this figure indexes the average correlation value computed between the pathway response curves G1, G2, and G3 of FIG. 2B and the drug response curves G1, G2, and G3, respectively, of FIG. 2A. It is well known in the art that, when two curves are identical, they will have a perfect correlation of 1.0. The horizontal axis indexes possible linear scaling parameters from 0 to 10. In this example, a perfect correlation value of 1.0 occurs at a scaling parameter of 2. The pathway response curves of FIG. 2B can be transformed with a linear scaling of 2 to fully match the drug response curves of FIG. 2A. Therefore, it can be concluded that the pathway originating at P1 is one of the pathways of action of drug D.

In order to determine whether the entire action of drug D can be explained by the pathways originating at P1 and P2, according to this invention the sum (the pathways are disjoint) of the both pathway responses (the response of the pathway originating at P2 is not illustrated) can be transformed into the response curves of all six genes to drug D.

For some embodiments of the invention, the response data may be interpolated. This interpolation is preferably accomplished either by spline fitting or by model-fitting. In spline fitting, the drug and pathway response data are interpolated by summing products of an appropriate spline interpolation function, S, multiplied by the measured data values, as illustrated by the following equations.

$$R_{i,k}(u) = \sum_1 S(u - p_{i,1})R_{i,k}(p_{i,1}) \qquad (1)$$

$$D_k(u) = \sum_1 S(u - t_1)D_k(t_1)$$

The variable "u" refers to an arbitrary value of the drug exposure level or the perturbation control parameter at which the drug response data and the pathway response data, respectively, are to be evaluated. In general, S may be any smooth (at least piece-wise continuous) function of limited support having a width characteristic of the structure expected in the response functions. An exemplary width can be chosen to be the distance over which the response function being interpolated rises from 10% to 90% of its asymptotic value. Different S functions may be appropriate for the drug and the pathway response data, and even for the response data of different pathways. Exemplary S functions include linear and Gaussian interpolation.

In model fitting, the drug and pathway responses are interpolated by approximating each by a single parameterized function. An exemplary model-fitting function appropriate for approximating transcriptional state data is the Hill function, which has adjustable parameters a, $u_0$, and n.

$$H(u) = \frac{a(u/u_0)^n}{1 + (u/u_0)^n} \qquad (2)$$

The adjustable parameters are selected independently for each cellular constituent of the drug response and for each cellular constituent of the pathway response. Preferably, the adjustable parameters are selected so that for each cellular constituent of each pathway response the sum of the squares of the distances of $H(p_{i,l})$ from $R_{i,k}(P_{i,l})$ is minimized, and so that for each cellular constituent of the drug response the sum of the squares of the distances of $H(t_l)$ from $D_k(t_l)$ is minimized. This preferable parameter adjustment method is known in the art as a least squares fit of $H()$ to $R_{1,k}()$ or to $D_k()$. Other possible model functions are based on polynomial fitting, for example by various known classes of polynomials.

Figure 3:
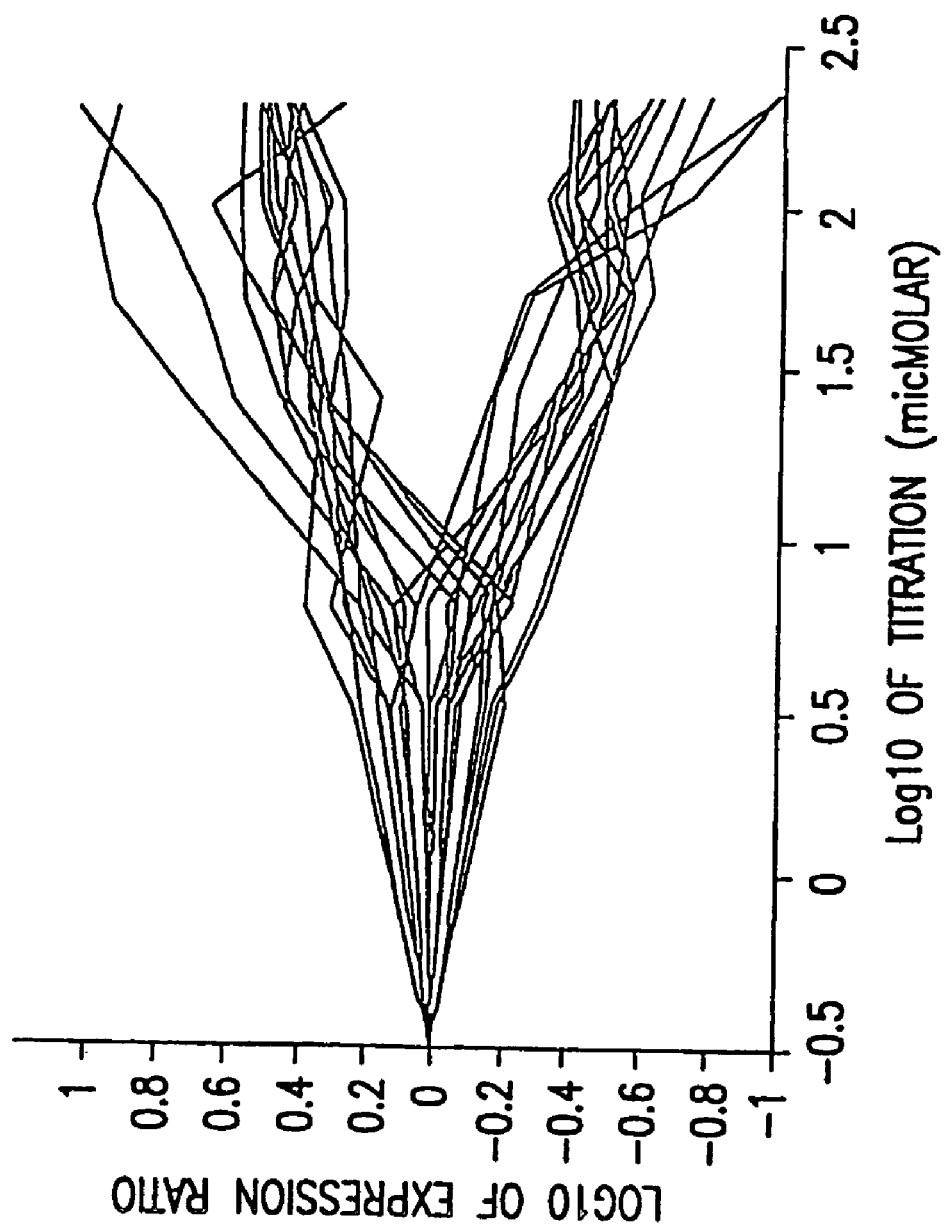
Figure 4:
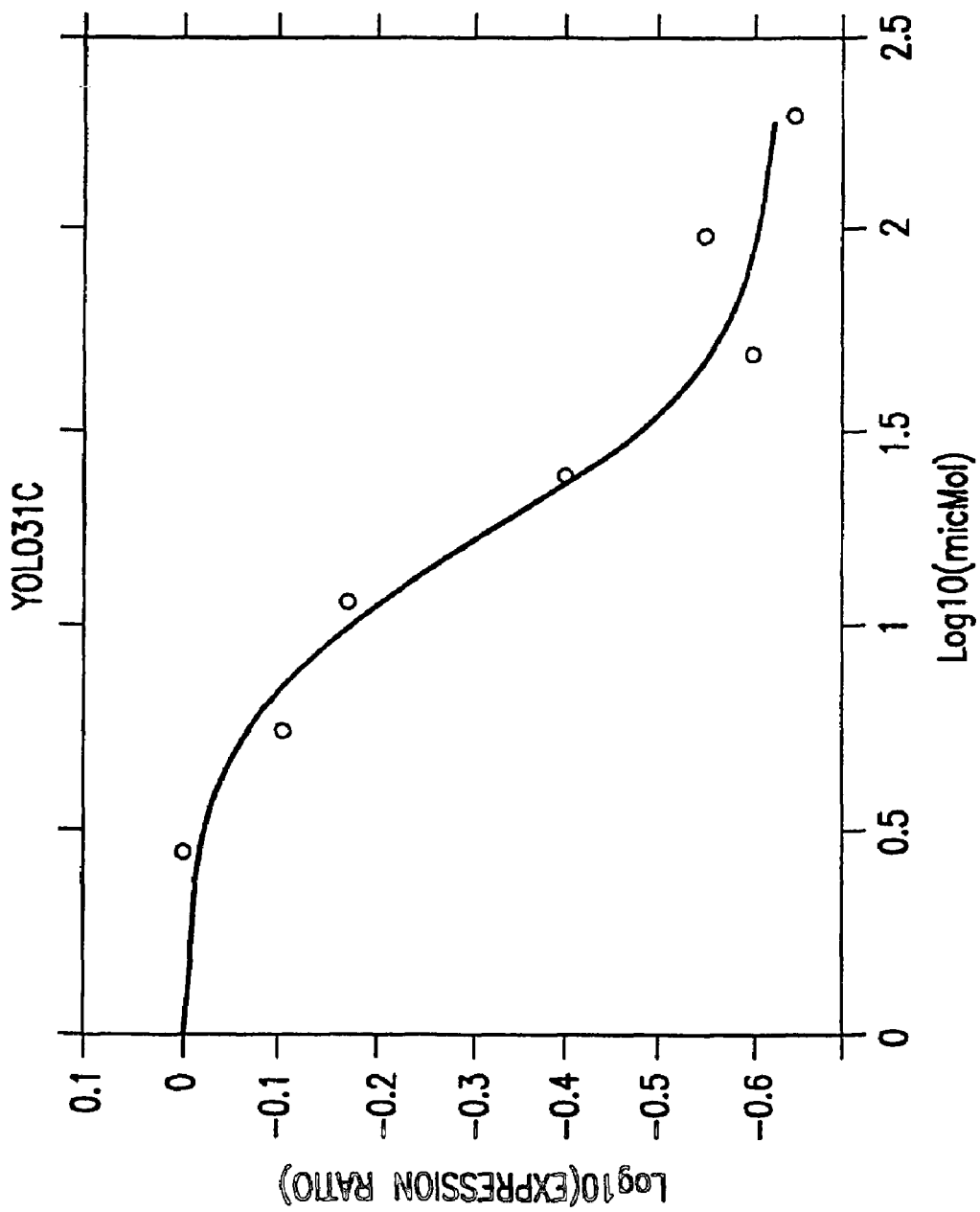
FIG. 4 illustrates the fit of a Hill function to the response of gene YOL031C illustrated in FIG. 3.

Model fitting with a Hill function is illustrated with respect to FIGS. 3 and 4. As discussed, FIG. 3 illustrates an example of a pathway perturbed by methotrexate and identified by measurement. This figure illustrates the mRNA expression levels of 30 genes of the yeast *S. cerevisiae* that, of the approximately 6000 genes in the genome of this yeast, had the largest expression changes in response to six different exposure levels of methotrexate. FIG. 4 illustrates a fit of the pathway response of one of these gene expression levels by a Hill function. In particular, the yeast gene YOL031C was fit by a Hill function with parameters n=2, a=−0.61, and $\log_{10}(u_0)$=1.26 selected by the previously described least squares method.

Since all of the 30 genes with largest responses behaved monotonically, i.e., none of the responses decreased significantly from its maximum amplitude (or increased significantly from its minimum amplitude) with increasing drug exposure, the Hill function is an appropriate model fitting function. For non-monotonic behavior it would not be.

After selection of a response data interpolation method, the last step prior to drug response data fitting, step 503, is the selection of a scaling transformation, along with any necessary parameters, which will relate the biological pathway responses to the drug responses. In general, a scaling transformation may need to scale vertically as well as horizontally. Vertical scalings may be necessary to relate the various measurements of the relevant characteristics of each cellular constituent made in acquiring the response data. For example, such measurements might be of abundances of mRNA species or activities of proteins. Where these measurements are made in commensurate units, vertical scalings are needed merely to relate the various units of measurement. Alternatively, where both drug and pathway measurements are made across a range of parameters from native levels to full saturation, as is preferable, these measurements can be scaled, for example, by the saturation values. Such scaling obviates the need for any vertical scaling. In this case, for example, where pathway responses are interpolated by fitting with a Hill function, the value of the parameter "a" for all response data will be substantially equal to 1. In the following, it is assumed that any necessary vertical scaling by saturation values has been done and that all pathway data vary between common native level and saturation values.

The analytic embodiments of the Pathway decomposition methods include, first, embodiments for representing drug response as a combination of pathway responses, and second, embodiments for assessing the statistical significance and verifying the results of the representation found.

Figure 5:
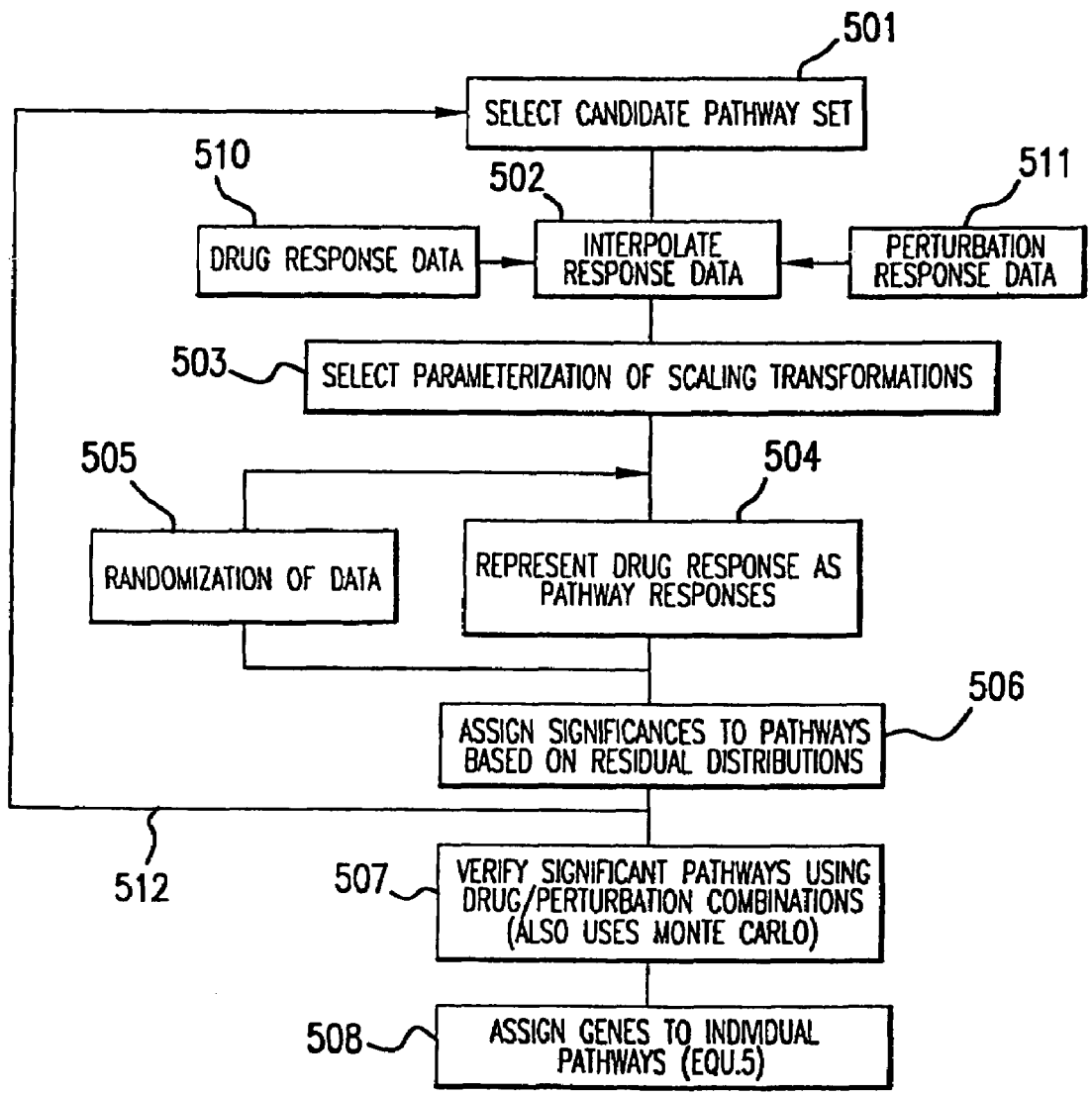
FIG. 5 illustrates a flow chart of one method for determining drug response of pathways.

FIG. 5 sets out a flow chart for a preferred embodiment of the methods of this invention. This embodiment determines a representative drug response data 510 for a particular drug in terms of pathway response data 511 for one or more pathways along with significance assessment and verification of the representation determined.

In other embodiments of this invention, certain steps illustrated in FIG. 5 may be omitted or performed in orders other than as illustrated. For example, in certain embodiments candidate pathway selection, step 501, and scaling parameterization selection, step 502, can be performed once for the analysis of the response data from several, preferably related, drugs and need not be performed for each drug analysis separately. Also, in particular embodiments, pathway significance assignment and verification may not be performed, and accordingly, one or more of steps 505 and 506, step 507, or step 508 may be omitted.

The representation of drug response data in terms of pathway response data preferably begins at step 501 with the selection of one or more candidate biological pathways with which to represent drug response data for a drug of interest. As discussed, the pathways preferably employed are those that originate at one or more cellular constituents, more preferably at constituents that are proteins likely to be targets of the drug of interest. Most preferably, the candidate pathways originate at single cellular constituents that are likely to be targets of the drug of interest.

Where candidate drug targets are not known, single pathways can be chosen from among available pathways, perhaps stored in a compendium of pathways, and tested for significance in representing the drug response data according to the following steps illustrated in FIG. 5. Those pathways individually found to have significance in representing drug response data can then be employed combined, and the steps of FIG. 5 performed in order to determine the best pathway combination for representing drug action. A compendium of pathways is preferably substantially complete in the biological system used for the assay (in that it includes substantially all biological pathways in that system), or at least includes substantially all pathways likely to be involved in drug action.

Pathway response data are measured in step 511 for the pathways selected in step 501. In many cases, for example, where a pathway has been defined by measurement, response data will already have been measured for perturbations to the selected pathways. In other cases, this response data must be measured prior to the succeeding steps of this invention. As described above, response data for a pathway includes measurements of relative changes in relevant characteristics of the cellular constituents present in the pathway for a plurality of control levels of a perturbation to the pathway. For example, where the pathway is defined by gene expression levels originating at a protein constituent, the activity of the originating protein can be perturbed in a graded manner and the resulting ratios (or logarithms of these ratios) of native to perturbed gene expression levels are measured. The perturbation control levels are preferably chosen so that five or more, or more preferably ten or more, perturbation control levels are present in the region where the characteristics of the cellular constituents rapidly change from native levels to saturation levels.

In the following, the variable "p" refers generally to perturbation control levels, and the variable "R" refers generally to the pathway response data. In detail, the l'th perturbation control level in the i'th biological pathway is referred to as "$p_{i,l}$". The pathway response for the k'th cellular constituent in the i'th pathway is $R_{i,k}$. Therefore, $R_{i,k}(p_{i,l})$ is the response of the k'th cellular constituent in the i'th pathway at the l'th level of the perturbation control parameter.

Similarly, drug response data are obtained in step 510, and must be measured if not already available. As described above, these data are obtained by measuring changes in characteristics of cellular constituents at a plurality of levels of drug exposure (also called herein "levels of drug titration"). As with pathway response data, the drug exposure levels (or "drug titrations") are preferably chosen so that five or more, or more preferably ten or more, exposure values are present in the region where the characteristics of the cellular constituents rapidly change from native levels to saturation exposure levels.

In the following, the variable "t" is used to refer generally to drug exposure (or "titration") levels, and the variable "D" refers generally to the drug response data. In detail, the l'th measured drug exposure level is referred to as "$t_l$". The drug response for the k'th cellular constituent is $D_k$. Therefore, $D_k(t_l)$ is the drug response of the k'th cellular constituent at the l'th level of drug exposure.

In the subsequent steps of these methods, in particular in step 504, values of the drug response data and the pathway response data may be needed at values of the drug exposure or perturbation control parameter which may not have been measured. This result follows from the fact that the measured drug exposure levels and pathway perturbation control parameters are not necessarily related. That is, for a particular l, the variables $t_l$ and $p_{i,l}$, for the various pathways, i, have no a priori relationship. Accordingly, it is necessary in step 502 to provide for interpolating of the various response data to obtain needed values. This interpolation method is preferably accomplished either by spline fitting or by model-fitting discussed above. The selection of an interpolation method and any necessary parameters are accomplished in step 502.

In general, horizontal scaling is expected to be necessary. As discussed above, such scaling is necessary because values of the perturbation control parameters for the various candidate biological pathways are likely not to cause saturation responses at the same numerical perturbation control values nor at the same numerical value as the saturation response of the drug exposure. For example, the pathway perturbations may act according to such entirely different mechanisms as the titration of a viral transfection vector expressing a protein from which a pathway originates, or the control parameter of a controllable promoter controlling expression of an originating protein, or the exposure level of a drug of specific known action on an originating protein. The saturating control values of these mechanisms, and indeed their kinetic characteristics, are likely to be all unrelated. All of these mechanisms may be different from the action of the drug of interest. For example, where perturbation action on a cellular constituent from which a pathway originates can be modeled as a Hill function, there is no reason that the various "$u_0$" parameters will be the same.

The preferred horizontal scaling transformation is a linear transformation of the drug exposure level into corresponding perturbation control parameters. An exemplary expression of such a transformation follows.

$$p_{i,l} = \alpha_i t_l + \beta_i \qquad (3)$$

Eqn. 3 provides the perturbation control value in the i'th pathway corresponding to the l'th drug exposure level. The linear scaling constants are $\alpha_i$ and $\beta_i$. Each pathway is characterized by one set of scaling parameters. Generally, $\beta_i$ will be 0 since both drug exposure and perturbation control values begin with zero. In essence, $\alpha_i$ represents a ratio of the strengths of the particular pathway perturbation to the drug of interest. For example, where the response data can be modeled as Hill functions, $\alpha_i$ is the ratio of the $u_0$ parameters of the drug of interest to that of the particular pathway.

More general horizontal scaling transformations are characterized by additional parameters. Flexible scaling transformations are possible with a number of parameters small enough, even though nonlinear, to be usefully employed in the minimization procedure of step 504. Multiple scaling parameters for the i'th pathway are represented herein by "$\alpha_i$". Another example of a scaling transformation is a polynomial expansion generalizing the linear transformation of Eqn 3. A simple example of a more general scaling transformation is the previously described Hill function employed according to the following equation.

$$P_{i,l} = \frac{\alpha_i (t_l/\mu_i)^{n_i}}{1 + (t_l/\mu_i)^{\gamma_i}} \qquad (4)$$

Again, Eqn. 3 provides the perturbation control value in the i'th pathway corresponding to the 1'th drug exposure level and is parameterized for each pathway by the three parameters $\alpha_i$, $\mu_i$, and $n_i$. The Hill function scaling is more general at least in that it reduces to a linear scaling when $n_i$ is 1 and $t_l$ is much less than $\mu_i$.

Step 504 is the central step of the methods of this invention in which the drug response is represented as a combination of appropriately scaled pathway responses. The preferred representation of the drug response is as a scaled linear combination of the pathway responses. Such a representation is particularly useful when the cellular constituents affected by one pathway are either unaffected by the other pathways, or have linearly additive effects if multiple pathways converge on the same cellular constituent, such as an mRNA or protein abundance. Since the convergence or overlap of pathways is most likely far downstream of the primary targets, where the influences have branched out to include many genes, the effects of multiple pathways are more likely to accidentally act as independent and additive effects. If the effects converged through a new cellular constituent in the two pathways, independence and additivity is less likely. In such cases, multiplicative cross-product terms could be included which would represent, inter alia, multiplicative responses of a cellular constituent resulting from convergence of multiple pathways at that cellular constituent. Even in the latter case and in other cases where linear additivity does not hold, errors introduced by the linear additivity can be corrected with the techniques of Section 5.3.1.

Therefore, preferably, the drug response data is represented in terms of the pathway response data according to the following equation.

$$D_k(t_l) \cong \sum_i R_{i,k}(\alpha_i, t_l); k = 1, K; l = 1, L \qquad (5)$$

Eqn. 5 represents the model drug response of the k'th cellular constituent at the l'th level of drug exposure in terms of the sum of pathway responses for the k'th cellular constituent scaled according to the selected transformation parameterized by the $\alpha_i$. It is understood that in general, here and subsequently, that the $R_{i,k}()$ are interpolated according to the methods of step 502, since it is rarely the case that measurements will have been made at the perturbation control values given by the scaled drug exposure levels. In cases where multiplicative cross-product terms are included (for example, in the cases previously described) Eqn. 5 would also include terms such as $R_{1,k}(\alpha_1, t_l) R_{i,k}(\alpha_i, t_l)$.

Sufficiently accurate solutions of this latter equation can be obtained by numerical approximation methods known in the art. These solution determine the best scaling transformation so that the model drug response matches the drug response as closely as possible. Preferred methods provide a numerical indication (herein referred to as a "residual") of the degree to which Eqn. 5 is not perfectly satisfied. According to a preferred method, pathway scaling parameters can be determined from the minimization of the related least squares approximation problem.

$$\min_{\{\alpha_i\}} \left\{ \sum_k \sum_l \left| D_k(t_l) - \sum_i R_{i,k}(\alpha_i; t_l) \right|^2 \right\} \qquad (6)$$

In Eqn. 6, the inner sum of the $R_{i,k}$ is over all interpolated pathway responses scaled according to the parameters $\alpha_i$ to correspond to the drug exposure level $t_l$. The parameters $\alpha_i$ for each biological pathway are generally a set of few parameters, such as from 1-5 parameters, defining the scaling transformation. The absolute square of the difference of this sum and the drug response at $t_l$ is in turn summed over all drug exposure levels, indexed by "l", and over all cellular constituents in the drug response or in the biological pathways, indexed by "k". The representation of the drug response in terms of the biological pathways is determined from the minimization of this latter sum with respect to the scaling transformation parameters for each pathway, the $\{\alpha_i\}$. The minimum value of this sum provides a numerical indication of the degree to which Eqn. 5 is satisfied, that is, the residual.

For linear scale transformations, Eqn. 6 has the following simpler form.

$$\min_{\{\alpha_i\}} \left\{ \sum_k \sum_l \left| D_k(t_1) - \sum_i R_{i,k}(\alpha_i t_1) \right|^2 \right\} \quad (7)$$

In Eqn. 7, each $\alpha_1$ is a single scaling constant for each biological pathway. Naturally, each $\alpha_i$ depends on the units chosen for the drug exposure and those chosen for the perturbation control value as well as on the actual physical relation between the potency of the drug and the potency of the perturbation method.

Minimization of least squares Eqns. 6 or 7 is performed using any of the many available numerical methods. See, e.g., Press et al., 1996, *Numerical Recipes in C*, 2nd Ed. Cambridge Univ. Press, Chs. 10, 14.; Branch et al., 1996, *Matlab Optimization Toolbox User's Guide*, Mathworks (Natick, Mass.). A preferred method is the Levenberg-Marquandt method (described in Press at al., Section 14.4). Since there are K genes, and L level of drug exposure, Eqns. 6 or 7 represent KL individual equations. The number of unknowns is equal to the number of hypothesized pathways times the number of scaling parameters per pathway. In the case of linear scaling, the number of scaling parameters equals the number of pathways. Typically, the number KL is much larger than the number of scaling parameters so that the least squares problem is considerably over-determined. Over-determination is advantageous in that it makes the solution robust, i.e., insensitive to measurement errors in individual cellular constituent responses.

An alternative to the least-squares procedure outlined in Eqns. 6 and 7 for solving Eqn. 5 is to maximize the normalized correlation between the model drug response and the measured drug response. This procedure is closely related mathematically to the least squares procedure. According to this procedure the $\alpha_i$ are determined from the solution to Eqn. 8.

$$\max_{\{\alpha_i\}} \left\{ \frac{\sum_k \rho_k(\alpha_i) A_{DK} A_{Rk}}{\left[ \left( \sum_k (A_{Dk})^2 \sum_{k'} (A_{Rk'})^2 \right) \right]^{1/2}} \right\} \quad (8)$$

In this equation, $\rho_k(\alpha_i)$ is the correlation coefficient between the drug response data for the k'th cellular constituent and the model pathway response for the k'th cellular constituent. In detail, this correlation coefficient is given by Eqn. 9.

$$\rho_k(\alpha_i) = \frac{\sum_l D_k(t_l) \left( \sum_i R_{i,k}(\alpha_i t_l) \right)}{\left[ \sum_m (D_k(t_m))^2 \sum_n \sum_i (R_{ik}(\alpha_i t_n))^2 \right]^{1/2}} \quad (9)$$

In Eqn. 9, the inner sum (over i) represents the model drug response for the k'th cellular constituent. The product of the model and measured drug responses are summed over all levels of drug exposure, and the sum is normalized by the root-mean-square (also called herein "RMS") values of the these responses to give the correlation coefficients. Returning to Eqn. 8, the values of the correlation coefficient are preferably normalized by the amplitudes $A_{Dk}$ and $A_{Rk}$, which are the response amplitudes for the measured and model drug responses for the k'th cellular constituents. These amplitudes are chosen to be RMS values of the measured and model drug responses over all levels of drug exposure. This normalization gives greater weight to cellular constituents with larger amplitude responses, while ensuring that perfect correlation gives a value of unity.

Alternatively and less preferably, the correlation coefficients can be unnormalized, in which case the amplitudes in Eqn. 8 are taken to be unity. Also, instead of the correlation coefficients, the negative of the correlation coefficients can be used, in which case the expression of Eqn. 8 is minimized (instead of maximized) to find the best scaling parameters.

Eqns. 8 and 9 can be solved by the methods described in the case of the least squares methods. It will be clear to those skilled in the art that the above fitting approach is equivalent to minimizing the negative value of Eqn. 8.

In both the least squares and the correlation methods, the summation of the pathway responses over the transformed drug exposure levels may lead to values outside of the measured interval of perturbation control parameters. This is because the scaling parameters, $\alpha_i$, can be substantially greater or less than unity. In order to avoid extrapolation of measured values, the sums in both cases (in Eqns. 6 and 8) are extended only over the interval in which there is measured data.

When drug responses from two different drugs are being compared, the steps outlined above in this section can be performed to generate a correlation coefficient, or, alternatively, a least squares residual, which is a measure of similarity of the effects of the two drugs. In such an embodiment, only one response pathway is scaled to fit the drug response data. Thus, in this particular embodiment the response R of the second "perturbation" drug is compared to the response data of the first drug D according to Eqn. 5, above, where K=1.

Following determination of a representation of the drug response as a combination of pathway responses, it is preferable, although optional, to assign a statistical significance to the pathway combination determined in step 506 and to verify the pathways determined to be significant in step 507.

Assessing Statistical Significance

Concerning step 506, the statistical significance of a pathway combination is determined by comparing the value of the minimum residual determined from the solution of Eqn. 5 to an expected probability distribution of residuals. The less likely the minimum residual is in terms of such a distribution, the more significant is the determined pathway combination. In the case of the correlation maximization method, the same methods can be applied to the maximum found in Eqn. 8. In particular, an expected distribution of this maximums can be found (as described below), and the significance of the actually obtained maximum determined from this distribution.

An expected probability distribution of residuals can be estimated by any method known in the art. Typically, this distribution is estimated analytically based on certain a priori assumptions concerning input probability distributions. Since such analytic estimation is difficult in this case, it is preferable to estimate the residual distribution by modeling based on a method described by Fisher. See, e.g., Conover, 2nd ed. 1980, *Practical Nonparametric Statistics*, John Wiley. This methods provides an empirical residual distribution by taking permutations or random subsets of the input data. In detail, here the input can be permuted with respect to the levels of drug exposure.

According to the preferred method, a residual distribution is constructed by repetitively solving Eqn. 5 with randomized input data and accumulating the residuals to form the empirical residual distribution. Thereby, the constructed empirical residual distribution arises from random data that has the same population statistics as the actual data. In detail, first, either the drug response data or the pathway response data (but not both) are randomized in step 505 with respect to the drug exposure levels or the perturbation control parameters, respectively. This randomization transformation is represented by the following transformation.

$$D_k(t_l) \leftarrow D_k(t_{\Pi(l)}) \tag{10}$$
$$R_{i,k}(p_{i,l}) \leftarrow R_{i,k}(p_{i,\Pi(l)})$$

In Eqn. 10, Π represents a permutation independently chosen for each cellular constituent. Either the drug response or the each pathway response (but not both) is randomized according to Eqn. 10. Accordingly, the randomized drug or pathway response data are derived from the measured data by independent permutations of the measurement points. Second, Eqn. 5 is then solved by the chosen numerical approximation technique in step 504 and the value of the resulting residual saved. These steps are repeated for enough randomizations to construct a sufficiently significant expected probability distribution of residuals. in order to obtain confidence levels of 99% or better (i.e., a P-value less than 0.01), then more than 100 randomizations are needed.

Having constructed the empirical residual distribution, in step 506, the actually determined residual is compared to the constructed distribution and its probability determined in view of that distribution. This probability is the significance assigned to the pathway. In other words, the statistical significance of any fit of a combination of pathways to the drug response is given in the preferred embodiment by the smallness of the probability value that randomized data are fit better by the assumed combination of pathways than the actual data.

In some cases, the pathway combination initially chosen in step 501 has adequate significance. For example, this is so if the pathway combination has at least the standard 95% probability threshold commonly used in medical sciences. If so, then this initial pathway combination can be verified in step 507 and cellular components assigned to individual biological pathways in step 508. In other cases, an acceptable significance threshold will not be met at first. If so, then, as indicated by arrow 512, it can be advantageous to return to step 501 and select a new set of candidate pathways in order to find a set meeting the chosen threshold standard of significance.

Accordingly, the assigned significance provides an objective method for assigning significance values and choosing between pathway combinations. This objective method of assigning significance allows meaningful identification of pathways from a large set of possible pathways likely to be involved in the action of a drug of interest, and provides an objective basis for halting the search for the additional pathways when the model drug response (possibly combining a plurality of pathways) attains sufficient objective significance.

In an alternative use of the significance as determined above, a single candidate pathway may be tested for significance according to two different approaches. In a first approach, the model drug response is taken to involve only that candidate pathway, and the pathway response data along that pathway are compared to the drug response data by correlation or least-squares residual (as described in Section 5.3.1). The significance of the fit, as determined by the randomization methods above, is compared to a threshold, such as the 95% threshold standard in the medical sciences, and the candidate pathway is taken to be a pathway of drug action if the significance is greater than that threshold.

In a second approach, the model drug response is assumed to involve multiple pathways, including the candidate pathway of interest. The pathway response data are then selectively randomized by randomizing only the pathway data for the candidate pathway according to Eqn. 10. The significance of the model drug response against this selectively randomized data is assessed by the previous methods. If this latter significance is significantly less than the former significance of the actual data, then the candidate pathway is taken to have significantly improved the model drug response. In that case, the pathway is likely to be a pathway of action of the drug of interest.

Verifying Pathway Combinations

Concerning next step 507, the representation of a drug response in terms of pathway responses can be independently verified by the preferred, but optional, steps described in this subsection. In the previous steps of this invention (steps 510 and 511), a biological system was perturbed either by drug exposure or by perturbations of selected pathways, but not by both drug exposure and pathway perturbations. In steps 504 and 506, the results of drug exposure were fit by a combination of the results of selected pathway perturbations, and then the statistical significance of this fit was estimated. Now in step 507, simultaneous drug exposure and perturbation of the significant pathways determined in step 504 are used to verify the that these pathways are indeed the actual pathways of drug action.

Figure 6:
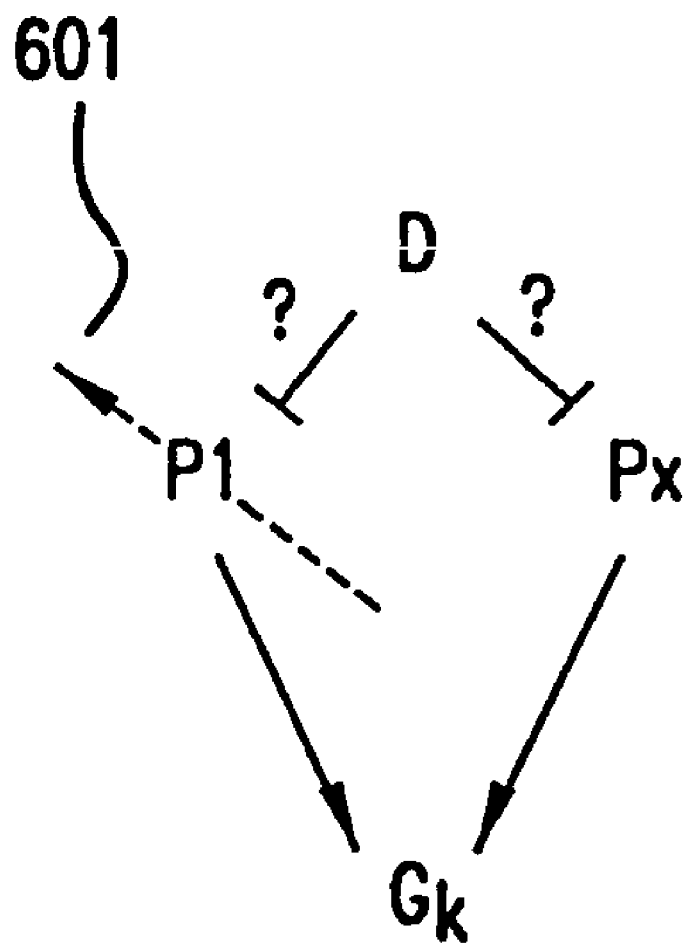
FIG. 6 illustrates possible alternative pathways for the action of drug D on Gene $G_k$.

Before describing the analytic details of pathway verification, the advantages of simultaneous drug exposure and pathway perturbation are exemplified with respect to the situation illustrated in FIG. 6. In FIG. 6, the expression of genes $G_k$ (for example, transcription state measurements of mRNA abundances) are affected by two pathways, one originating at protein P1 and the other at protein Px. Drug D is assumed to act on genes $G_k$ either by inhibiting P1 or by inhibiting Px. If the inhibitory perturbations to the two pathways produce similar responses in the genes $G_k$, then even if drug D acts only by inhibiting Px, its drug response will be well fit in step 504 by inhibitory perturbation 601 to the pathway originating at P1, and this pathway may be incorrectly identified as being the likely pathway of action of drug D. This error can be remedied by simultaneous exposure to drug D and inhibition of P1 or of Px. Exposure to drug D and inhibition of P1 will not result in a changed drug response, since the drug response is in fact mediated via Px. However, exposure to drug D and inhibition of Px will result in a changed drug response, since both the drug and the perturbation now act at Px. The different responses to simultaneous drug exposure and pathway perturbation in these two cases allow the correct pathway of action of drug D to be unambiguously identified.

The general description of verification step 507 begins, first, with consideration of case where only one pathway is involved in representing the drug response, and follows with consideration of the general case of multiple pathways. In the following, as previously, $D_k(t_l)$ refers to the response of the k'th cellular constituent to the l'th level of drug exposure, and $R_{i,k}(p_{i,l})$ refers to the response of the k'th cellular constituent in the i'th pathway in response to the l'th level of the appropriate perturbation control parameter. Further, the variable DR refers to the results of the combined exposure of the biological system to both the drug and to a pathway perturbation. In detail, $DR_{i,k}(p_{i,l},t_m)$ refers to the response of the k'th cellular constituent in the i'th pathway in response to the l'th level of the appropriate perturbation control parameter and to the m'th level of drug exposure.

In the case of a single pathway of drug action, if the drug indeed acts on that pathway then the combined response, DR, is given by the following.

$$DR_{i,k}(p_{i,l},t_m) = R_{i,k}(p_{i,l} + \alpha_i t_m) \tag{11}$$

where $\alpha_i$ is the best scaling parameter determined for this pathway. A linear scaling is assumed here; adaptation to more general scaling transformations is apparent from the preceding description. DR has the foregoing form because, in this case, both the drug and the perturbation act on the same constituents of the pathway, in particular on their originating constituents, and the response of the pathway is due to the summed effect.

The behavior of Eqn. 11 is illustrated in FIG. 7A, where, for purposes of example only, D and R have been modeled by the Hill function. Characteristically, the function DR in this case saturates at substantially the same values for large drug exposure (drug "titrations"), near asterisk 701, for large perturbation, near asterisk 702, and for the combination of large drug exposure and large perturbations, near open circle 703.

If, instead, the drug acts on a different pathway, not on the i'th pathway, then the combined response, DR, is given by the following.

$$DR_{i,k}(p_{i,l},t_m) = R_{i,k}(p_{i,l}) + D_k(t_m) \tag{12}$$

The response has this form in this case because the drug acts only on cellular constituents outside of the i'th pathway. Since the pathway perturbation is limited to cellular constituents in the i'th pathway, it acts independently of the drug. Consequently, the action of the drug and the perturbation are independent and their effects are additive on cellular constituents. (The effects may be combined as needed according to the other combination functions discussed in Section 5.2)

The behavior of Eqn. 12 (assuming $\alpha_i$ equals 1) is illustrated in FIG. 7B, where, for purposes of example only, D and R have again been modeled by the Hill function. In this case, the function DR saturates at substantially the same values for large drug exposure (drug "titrations"), near asterisk 704, and for large perturbation, near asterisk 705. But for the combination of large drug exposure and large perturbations, this function reaches substantially higher values near open circle 706 than at either asterisks 704 or 705, where only the drug exposure or the perturbation alone is saturating.

Clearly, it is possible to distinguish the cases represented by FIGS. 7A and 7B by performing experiments for verification conditions where both the drug exposure and the pathway perturbation are simultaneously present. Such experiments are preferably at drug exposure and perturbation values represented by the open circles in FIGS. 7A and 7B, and most preferably at open circles 703 and 706. Less preferably, these experiments are performed at values in the interior of the surfaces illustrated in these figures, especially in the region bounded by lines between asterisks 701 and 702 and open circle 703 in FIG. 7A, and in the region bounded by lines between asterisks 703 and 704 and open circle 705 in FIG. 7B. It is also clear that it would not be possible to distinguish these cases solely by performing experiments in which only one of the drug exposure or perturbation control values are non-zero. The curves in FIG. 7A between asterisk 710 and either asterisk 701 or asterisk 702 are substantially the same as the curves in FIG. 7B between asterisk 711 and either asterisk 704 or asterisk 705.

In summary, the identification of the i'th pathway as the pathway of drug action is verified if experimental results more closely resemble FIG. 7A than FIG. 7B.

Considering the case of multiple pathway in general, $TR_k(p_{1,l},t_m)$ refers to the total response of the k'th cellular constituent in response to the l'th level of the appropriate perturbation control parameter in the i'th pathway and to the m'th level of drug exposure. TR is given by the following equation if the drug acts through the indicated pathways.

$$TR_k(p_{i,l}, t_m) = \sum_i DR_{i,k}(p_{i,l}, t_m) = \sum_i R_{i,k}(p_{i,l} + \alpha_i t_m) \tag{13}$$

TR is given by the following equation if the drug does not act through the indicated pathways.

$$TR(p_{i,l}, t_m) = \sum_i DR_{i,k}(p_{i,l}, t_m) = \sum_i (R_{i,k}(p_{i,l}) + D_k(t_m)) \tag{14}$$

An objective choice between these two possibilities can be made in a manner similar to the statistical confidence estimation method described in the previous subsection. Values for $TR_k(p_{1,l},t_m)$, the left-hand side of Eqns. 13 and 14, are experimentally determined for various preferred verification conditions, and values for the right-hand side are computed from the measurements of the drug response and the pathway responses in steps 510 and 511 and from the determination of the optimum scaling parameters in step 504. The residuals for these equations, that is the sum of the squares of the differences of the left- and right-hand sides, are then computed. Without more, the alternative with the lesser residual is the objective choice.

The statistical significance of the residuals can be estimated by, first, estimating a probability distribution of residuals. The estimated residual probability distribution is determined by repeatedly randomizing the right hand sides of Eqns. 13 and 14 with respect to the perturbation control parameter index and the drug exposure index and then recomputing the residuals. The statistical significance of the actual residuals are then determined with respect to this model probability distribution.

Typically, only a small number of verification conditions are needed to confirm with significance the existence of a pathway which was determined to be significant in step 506.

In final optional step 508, after drug responses have been represented as a combination of pathway responses in step 504 and best-fit scaling parameters have been accordingly determined, each affected cellular constituent can be assigned to the pathway with which its drug response is most correlated. Optionally, the pathways have also been declared significant in step 506 based, for example, on a significance threshold, such as the standard 95% probability threshold often used in the medical sciences. For the k'th cellular constituent its drug response, $D_k(t_l)$, is correlated with the individual response of that constituent in the response data of each pathway.

$$\rho_{i,k} = corr(D_k(t_l)R_{i,k}(\alpha_i t_l)) \quad (15)$$

$$= \frac{\sum_l D_k(t_l)R_{i,k}(\alpha_i t_l)}{\left[\sum_m (D_k(t_m))^2 \sum_n (R_{ik}(\alpha_i t_n))^2\right]^{1/2}}$$

In Eqn. 15, $\rho_{i,k}$ is the correlation of the drug response of the k'th cellular constituent with its response in the i'th pathway. The k'th cellular constituent is assigned to the i'th pathway where $\rho_{1,k}$ is larger than $\rho_{l,k}$ for all l not equal to i. Similarly to the previous significance estimations, the statistical significance of this correlation can be determined by randomizing the drug response data in Eqn. 15.

5.2. PATHWAY ACTIVITY REPRESENTATION

In the previous section (see, e.g., Eqn 5), the drug activity on a cellular constituent (k) is generally decomposed into pathway activity on the cellular constituent k:

$$D_k(t_l) \cong \sum_i R_{i,k}(\alpha_i, t_l); \quad (16)$$

Where $D_k(t_l)$ is the drug activity on cellular constituent k when the drug is applied at a level $t_l$; $R_{i,k}(\alpha_i, t_l)$ is the response of cellular constituent k in pathway i under perturbation ($\alpha_i$, $t_l$) (for the scaling transformation of perturbation levels using parameter $\alpha_i$, see section 5.1, supra, or U.S. patent application Ser. No. 09/074,983, filed on May 8, 1998, now U.S. Pat. No. 5,965,352, previously incorporated by reference). $R_{i,k}(\alpha_i, t_l)$ represents the drug activity on the cellular constituent in pathway i. Drug activity on a cellular constituent k in pathway i is represented as:

$$D_{i,k}(t_l) = R_{i,k}(\alpha_i, t_l) \quad (17)$$

In this representation, the drug activity on a particular pathway is represented by drug activity on a number of individual cellular constituents. Using the hypothetical pathways in FIG. 1 as an example, the drug activity on pathway 102 is represented by the drug activity on cellular constituents P2, P3, G1, G2, G3, etc.

For some embodiments of the invention, the drug activity on a particular pathway is more conveniently represented by a single parameter, rather than a group of responses of cellular constituents. In some preferred embodiments, the drug activity on pathway i, when the drug is applied at the level $t_l$, is represented by:

$$D_i(t_l) = \sum_k \beta_k R_{i,k}(\alpha_i, t_l) \quad (18)$$

Where $\beta_k$ is a constant for cellular constituent k. One of skill in the art would appreciate that the selection of constant $\beta_k$ is dependent upon the unit used in measuring cellular constituent responses. For example, if a cellular constituent response measurement is the activity of an enzyme, while another cellular constituent response measurement is a gene expression ratio, two different β constants can be assigned to the two different cellular constituent types to adjust the difference in units and ranges of the measurements. Selection of the constants in a linear transformation to take account for different units of measurements and different range of variables is well within the skill of those in the art. In one particularly preferred embodiment, where the response of all cellular constituents are measured as the expression ratios (expression under perturbation over expression without perturbation), the $\beta_k$ is given the value of 1.

The above representation of the drug activity is dose (in vivo) or concentration (in vitro) dependent, i.e., a particular drug activity is applicable only when the specific dose or concentration is applied. In some preferred embodiments, a single parameter is used to represent the drug activity on a particular pathway. In some such embodiments, the drug activity on a particular pathway is represented by the minimal level ($C_i$) of the drug needed to achieve certain threshold response in a particular pathway, i.e.:

$C_1$=minimal level of a drug to achieve a threshold response; (19)

When gene expression levels are measured, the threshold response may be defined as more than two fold, preferably more than three fold, more preferably more than 10 fold, of induction or repression of gene expression. For example, if a minimum of 0.5 μg/mL of a drug is needed to achieve a two fold induction or suppression of all the genes in a first pathway, the activity of the drug on the first pathway can be represented by the minimum level of 0.5 μg/mL. Similarly, if a minimum of 1.0 μg/mL of the same drug is needed to induce or repress all the genes in a second pathway, the activity of the drug on the second pathway can be represented by the minimum level of 1.0 μg/mL. According to such a representation, the drug has a higher activity on the first pathway then the second pathway, because of the lower minimum level for the first pathway.

Because not all cellular constituents in a pathway respond in a similar fashion and the range of response of each cellular constituent in one pathway may vary in its range, different threshold levels can be set for different cellular constituents. One particularly preferred embodiment uses the number of cellular constituents induced or repressed. For example, if a minimum level of a drug is needed to induce or repress more than 10%, preferably more than 20%, more preferably more than 90% of the cellular constituents in a particular pathway for more than two fold, preferably more than three folds, more preferably more than 10 fold, the minimum level may represent the activity of the drug on the particular pathway.

The threshold levels may also be set according to the biological function of the particular pathways. For example, if a biological pathway is known to suppress immune responses if some of its genes are induced for more than two-fold, the drug activity (therapeutic activity) for the biological pathway may be represented by the minimum level of the drug required to induce or suppress those genes. Similarly, if an induction of more than two fold of cellular constituents of a pathway outside the target of a drug indicates potential toxicity (See the following sections), the threshold of two fold induction or repression may be set as a toxic response and the minimum level of the drug needed to achieve the two fold induction or repression may be used to indicate the drug activity (toxic) on the particular pathway.

5.3. EVALUATION OF RELATIVE EFFICACY AND TOXICITY OF A DRUG

One aspect of the invention provides methods for determining the specificity index (SI) of a drug in an in vitro system, based upon the drug's activity on target versus off-target pathways. The target and off-target pathways are previously discussed, for example, in Section 5.1, supra. The specificity index measurements is particularly useful to evaluate the relative efficacy and toxicity of a drug candidate during the early phase of drug screening. Specificity index is defined herein as the relative activity of a drug against its primary target pathway versus its activity against "off target" pathways. Methods for determining the activities of a drug on different pathways have been described in detail in the Sections 5.1 and 5.2, supra. Some of the methods are also described in Stoughton and Friend, Methods for Identifying Pathways of Drug Action, U.S. patent application Ser. No. 09/074,983, filed on May 8, 1998, now U.S. Pat. No. 5,965,352, incorporated previously by reference for all purposes. One of skill in the art would appreciate that the some methods of the invention are limited by particular methods for detecting "on-target" or "off-target" activities of a drug.

In one embodiment, the specificity of a drug is evaluated using a specificity index SI) defined as:

$$SI = \frac{n \cdot D_{target}}{\sum D_{off-target}} \quad (20)$$

Wherein $D_{target}$ is the response of the target pathway to the drug (or the activity of a drug on its target pathways); $D_{off-target}$ is the response of an off-target pathway to the drug (or the activity of drug on the off-target pathway); n is the number of off-target pathways examined. It is sometimes preferable to include only off-target pathway(s) that may be involved in adverse events.

The drug activity of the target pathway ($D_{target}$) and off target pathways ($D_{off-target}$) may be represented as response of individual cellular constituent as in Eqn (17) or as response of the pathway as in Eqn (18). The response may also be in a dose dependent fashion ($D_{target}(t_l)$ and $D_{off-target}(t_l)$) as in Eqns 17 and 18 or in a dose independent fashion (such as 19).

The specificity index of a drug is particularly useful for the selection of drug candidates at the early stage of a drug discovery process (such as for an in vitro screening process).

The specificity indexes of drug candidates are determined using an in vitro model system. A low specificity index indicates relative small activity on the target pathway vs. activity on off-target pathways. The drug candidates with low specificity indexes are eliminated from the candidate list, because of the likelihood of off-target activity or toxicity.

5.4. THERAPEUTIC INDEX PREDICTION

As discussed in Section 2, Background of the Invention, supra, therapeutic index is defined as either as the ratio of the $TD_{50}$ of an undesirable or limiting side effect to the $ED_{50}$ (medium effective dose) for the desired therapeutic effect or the ratio of the $LD_{50}$ (median lethal dose) to the $ED_{50}$. A therapeutic index provides a simple index for evaluating the safety and efficacy of a drug.

In one aspect of the invention, the drug activity on a target ($D_{target}$) and off-target ($D_{off-target}$) pathways are determined to estimate in vitro and in vivo therapeutic indexes. In such embodiments, the therapeutic index (TI) is defined as:

$$TI = \frac{C_{off-target}}{C_{target}} \quad (22)$$

Wherein $C_{off-target}$ is the concentration of the drug above which a response of off-target pathways reaches a threshold; $C_{target}$ is the concentration of the drug above which a response of target pathways reaches a threshold.

A threshold definition allows objective comparison of the therapeutic index for alternative drugs (such as drugs used to affect the same target pathway) in a model system. One of skill in the art would appreciate that the thresholds can be determined based upon the model system and particular pathways involved. In some embodiments, assignment of the threshold value is based upon clinical experience of similar drugs in the past, such threshold value setting is well within the ordinary skill of an artisan.

Even though it may be difficult to extrapolate a therapeutic index obtained from a model organism to the human or other target systems, the therapeutic index of a particular drug candidate relative to alternative drugs should be indicative of the ranking of those drugs in the target systems, especially when off-target effects of those drugs are similar.

In one preferred method, the threshold is set according to the relationship between toxicity and the pathways involved. For example, if a particular concentration of a drug that induces a particular off target pathway by two-fold in a model system (such as a yeast model system) and later the drug is found to have toxicity when administered to a patient population at a dose that is equivalent to the concentration, the toxicity threshold may be set as two fold induction for this particular pathway. Similarly, if a particular concentration of a drug that represses a particular target pathway by three folds in a model system and later the drug is found to have a desired therapeutic effect in a patient administered with a dose that is equivalent to the concentration, the therapeutic threshold can be set as three-fold of repression for the particular target pathway.

In one particularly preferred embodiment, the response of pathways to a drug is determined by the expression of the genes in the pathways. In this embodiment, the target or off target pathway responses reach the threshold when expression of most of the genes is induced or repressed by two-fold.

Example 1 (Section 6, infra) illustrates one such embodiment. In this example, the expression of a number of genes are monitored as a wild type yeast culture is subjected to a graded levels of the drug FK506 (FIG. 8A). Similar experiments are repeated with a yeast culture whose CNA1 and CNA2 genes are deleted (FIG. 8B). CNA1 and CNA2 are two components of the calcineurin multi-protein complex. Because the drug FK506 acts upon the calcineurin protein to exert its activity on the calcineurin pathway. Deletion of CNA1 and CNA2 eliminates the primary target pathway for FK506. For a discussion of the yeast model system, see, Cardens et al., 1994, "Yeast as Model T Cells, Prosp. In DRUG DISCOVER. DESIGN, 2:103-126.

FIG. 8A shows that the expression of the most of the genes affected via the primary target, the calcineurin pathway (those genes that do not respond in the absence of the calcineurin pathway), reaches two fold induction or repression at the concentration of 0.2 µg/ml. The expression of most off-target genes (represented by bold dash lines) reaches two fold induction or repression at the concentration of 12 µg/ml. The therapeutic index is for this drug in the yeast model is therefore 12/0.2=60.

Therapeutic index data obtained from cell culture assays and/or animal studies can be used in predicting the therapeutic index in vivo and formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, In: *The Pharmacological Basis of Therapeutics*, Ch. 1 p1).

5.5. DRUG THERAPY MONITORING

As discussed in the background section, clinical toxicity signs are difficult to detect. Drug effect or toxicity may not show up as clinical signs before it is too late to make a informed therapeutic decision. The drug response of at least some pathways, however, are relatively faster. Accordingly, this invention provides methods for evaluating the drug effect or toxicity in a patient that undergoes drug therapy using pathway activities rather than clinical signs or individual cellular constituent changes.

In some embodiments, the expression of a large number of genes in the patient (a human or an animal) is determined while the patient undergoes therapy. The drug responses of the primary target pathway and off-target pathways are determined according to the methods of the invention and other suitable methods. If a patient's primary target pathway does not respond to the drug therapy and/or the off target pathways respond strongly to the drug therapy, the therapy may be discontinued in favor of alternative treatments. Because the drug response of pathways can sometimes be determined earlier than clinical signs, the method of the invention offers the advantage that clinical decision can be made before clinical toxicity and therapy failure is detected by clinical signs.

5.6. DRUG EFFICACY AND TOXICITY EVALUATION FOR INDIVIDUALS

Another aspect of the invention provides methods for determining individual variations in drug response. These methods are particularly useful in selecting drug therapy plan and dose calculation for a particular individual.

In some embodiments, the expression of a large number of genes in a patient is monitored as the patient receives a plurality of perturbations. The perturbation can be a particular drug given at different doses. The drug responses of the target and off target pathways are determined according to the method of invention and other suitable methods. Suitable dosage can be determined so that the drug elicits a strong drug response in the target pathways and a relatively weak response in the off target pathways. If a strong response in off target pathways is illicit, the drug is determined to be unsuitable for the particular patient.

In such embodiments, clinical toxicity can be avoid by closely monitoring the drug response of off target pathway. A strong drug response of off target pathways may be detected before clinical toxicity develops.

In some embodiments, the specificity index and therapeutic index of a drug for individual patients may be estimated by perturbing the patients with different levels of perturbation and the drug. A large number of cellular constituents are measured. The drug response is decomposed into pathway responses according to the methods described in Sections 5.1 and 5.2, supra. The specificity index and therapeutic index are estimated using the methods described in the above sections.

5.7. COMPUTER IMPLEMENTATION

The analytic methods described in the previous subsections can preferably be implemented by use of the following computer systems and according to the following programs and methods. FIG. 9 illustrates an exemplary computer system suitable for implementation of the analytic methods of this invention. Computer system 901 is illustrated as comprising internal components and being linked to external components. The internal components of this computer system include processor element 902 interconnected with main memory 903. For example, computer system 901 can be an Intel Pentium®-based processor of 200 Mhz or greater clock rate and with 32 MB or more of main memory.

The external components include mass storage 904. This mass storage can be one or more hard disks (which are typically packaged together with the processor and memory). Such hard disks are typically of 1 GB or greater storage capacity. Other external components include user interface device 905, which can be a monitor and keyboard, together with pointing device 906, which can be a "mouse", or other graphic input devices (not illustrated). Typically, computer system 901 is also linked to network link 907, which can be part of an Ethernet link to other local computer systems, remote computer systems, or wide area communication networks, such as the Internet. This network link allows computer system 901 to share data and processing tasks with other computer systems.

Loaded into memory during operation of this system are several software components, which are both standard in the art and special to the instant invention. These software components collectively cause the computer system to function according to the methods of this invention. These software components are typically stored on mass storage 904. Software component 910 represents the operating system, which is responsible for managing computer system 901 and its network interconnections. This operating system can be of the Microsoft Windows™ family, such as Windows 95, Windows 98, or Windows NT. Software component 911 represents common languages and functions conveniently present on this system to assist programs implementing the methods specific to this invention. Languages that can be used to program the analytic methods of this invention include C and C++, or JAVA®. Most preferably, the methods of this invention are programmed in mathematical software packages which allow symbolic entry of equations and high-level specification of processing, including algorithms to be used, thereby freeing a user of the need to procedurally program individual equations or algorithms. Such packages include Matlab from Mathworks (Natick, Mass.), Mathematica from Wolfram Research (Champaign, Ill.), or S-Plus from Math Soft (Seattle, Wash.).

In an exemplary implementation, to practice the methods of this invention, a user first loads drug response data and pathway response data into computer system 901. These data can be directly entered by the user from monitor and keyboard 905, or from other computer systems linked by network connection 907, or on removable storage media (not illustrated). Next, the user causes execution of drug response representation software 912, after optionally supplying initial pathways of interest, followed by execution of significance assessment software 913. Thereby, the user obtains a model drug response and its statistical significance.

Alternative systems and methods for implementing the analytic methods of this invention will be apparent to one of skill in the art and are intended to be comprehended within the accompanying claims. In particular, the accompanying claims are intended to include the alternative program structures for implementing the methods of this invention that will be readily apparent to one of skill in the art.

6. EXAMPLE: THERAPEUTIC INDEX OF FK506

The invention having been described, the following example is offered by way of illustration and not limitation. This example illustrates the estimation of therapeutic index for FK506 using a yeast culture model.

6.1. METHODS AND MATERIALS

An overnight starter culture of *S. cerevisiae* strain R563 (Genotype: Mat a ura3-52 lys2-801 ade2-101 trp1-Δ63 his3-Δ200 leu2-Δ1 his3::HIS3) was diluted into 200 of YAPD plus 10 mM $CaCl_2$ medium (see, e.g., Ausubel et al., eds., 1996, *Current Protocols in Molecular Biology*, John Wiley & Sons, Inc., especially ch. 13) to an $OD_{600}$ of 0.1 and grown at 30° C. with 300 rpm shaking. After a 30 min, FK506 dissolved in ethanol was added to cultures at final concentrations of 0.10, 0.31, 1.0, 1.6, 5.0 16.0, 50 μg/ml.

Control cultures were treated with the same volume of just ethanol. Growth was monitored by $OD_{600}$ and cells were harvested at $OD_{600}$=1.4+/−0.1 by centrifugation for 2 min at ambient temperature in a Sorvall RC5C+ centrifuge in a SLA-1500 rotor. The supernatant was discarded, the residual liquid removed by pipetting, and the cells were resuspended in 4 ml RNA Extraction Buffer (0.2M Tris HCl pH 7.6, 0.5M NaCl, 10 mM EDTA, 1% SDS). Cells were vortexed for 3 sec to resuspend the pellet and then immediately transferred to 50 ml conical centrifuge tubes containing 2.5 g baked glass beads (425-600 μM) and 4 ml phenol:chloroform (50:50 v/v). Tubes were vortexed for 2 min in the VWR Multi-tube Vortexer at setting 8 prior to centrifugation at 3000 rpm for 5 min at ambient temperature in a Sorvall Model T600D tabletop centrifuge to separate the phases. The aqueous phase was reextracted with equal volume of phenol:chloroform (50:50 v/v) by vortexing for 30 sec at setting 6 followed by centrifugation as before. To the aqueous phase was added 2.5 volumes of ethanol and the samples were stored at −80° C. until isolation of polyA$^+$ mRNA.

In all cases, polyA$^+$ RNA was isolated by oligo-dT cellulose chromatography using two selections by standard protocols (see, e.g., Sambrook et al. 1989, *Molecular Cloning A Laboratory Manual*, Cold Spring Harbor Laboratory Press). Two micrograms of polyA$^+$ RNA was used in reverse transcription reactions. cDNA was purified and hybridized to polylysine slides.

Extent of hybridization was determined by scanning with a prototype multi-frame CCD camera slides produced by Applied Precision, Inc. Images were processed by informatics and imported into the Inpharma database and analyzed using the MatLab data analysis package.

6.2. RESULTS

Table 1 shows the off-target genes identified by titration in deletion strain. The response of those genes to FK506 were considered as off-target activity. Each ORF (Open Reading Frame) may be corresponding to an off-target gene.

TABLE 1

| OFF-TARGET GENES IDENTIFIED BY TITRATION IN DELETION STRAINS. | |
|---|---|
| ORF | Log10(Ratio) |
| YER175C | 1.0121 |
| SNZ1 | 0.9834 |
| ARG1 | 0.9516 |
| ARG5,6 | 0.9136 |
| YGL117W | 0.8608 |
| HIS5 | 0.8266 |
| HIS4 | 0.8178 |
| ECM13 | 0.8176 |
| ARG4 | 0.7774 |
| SNO1 | 0.7711 |
| YMR085W | 0.7679 |
| RIB5 | 0.7436 |
| YOL150C | 0.7246 |
| GRE2 | 0.6836 |
| SNQ2 | 0.6624 |
| CPA2 | 0.645 |
| YOR203W | 0.6378 |
| ARO3 | 0.6261 |
| HIS3 | 0.6152 |
| YMR097C | 0.6945 |
| PDR5 | 0.597 |
| YOR1 | 0.5928 |
| CPA1 | 0.5645 |
| YHM1 | 0.5235 |
| NCE3 | 0.5112 |
| YPL088W | 0.4764 |

FIGS. 8A-C illustrate the drug response data generated by a series of FK506 exposures. The horizontal axis is concentrations of the FK506 in logarithmic scale and the vertical axis is the values of the logarithm of the expression ratio of the genes most affected by FK506 on the vertical axis. FIG. 8A shows the transcriptional response of the yeast genome to a titration of the drug FK506. FIG. 8A shows the transcriptional response in a in different experiment when the drug is applied to a yeast strain in which both components of the calcineurin protein have been removed by deletion of the genes CNA1 and CNA2. Plotted genes have P-Value<0.03 and abs(Log10(expression ratio))>0.3 at two or more concentrations in the series. P-Value is the probability that the up or down regulation is due to measurement error, as determined from observed statistics of the errors in Log10(expression ratio).

The transcriptional response in FIG. 8B is 'off-target' in the sense that the response must be independent of the primary therapeutic effect of FK506, an immunosuppressant, which is via inhibition of the calcineurin protein via the action of the complex of FK506 with its ligand FK506 binding protein (Cardenas, et al., 1994, Yeast as model T cells, in PERPECTIVES IN DRUG DISCOVERY AND DESIGN, 2:103-126). Although the relation with actual clinical toxicity is not direct, a toxic concentration may be defined as the concentration at which the 'off-target' transcriptional responses of many genes reach two-fold induction or repression. This concentration is given by inspection of FIG. 8B, and is approximately 12 mg/ml. The responses in FIG. 8A result from the combined effects of FK506 via calcineurin and the effects via other pathways in which the responses of those genes which respond in the calcineurin-deleted strain are represented by bold dashed lines. The responses represented by smooth lines are those via the primary pathway (calcineurin). These responses achieve twofold induction or repression at concentration about 0.2 mg/ml. The therapeutic index for this drug in this system is therefore estimated to be about 12/0.2=60. FIG. 8C is the same as FIG. 8A except for that the threshold values are indicated.

7. REFERENCES CITED

All references including patent applications and publications cited herein are incorporated herein by reference in their entirety and for all purposes to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art. The specific embodiments described herein are offered by way of example only, and the invention is to be limited only by the terms of the appended claims, along with the fall scope of equivalents to which such claims are entitled.

What is claimed is:

1. A method for evaluating specificity of a drug comprising:
   a) comparing activity of a drug against its target pathway ($D_{target}$) in a biological sample and activity of said drug against at least one of its off-target pathways ($D_{off\text{-}target}$) in said biological sample, wherein said $D_{target}$ and $D_{off\text{-}target}$ are represented by quantities selected from the group consisting of (i)
   $$D_{target} = R_{target,k}(\alpha_{target}, t_l) \text{ and}$$
   $$D_{off-target} = R_{off-target,k}(\alpha_{off-target}, t_l), \text{ respectively;}$$

(ii)
   $$D_{target} = \sum_k \beta_k R_{target,k}(\alpha_{target}, t_l) \text{ and}$$
   $$D_{off-target} = \sum_k \beta_k R_{off-target,k}(\alpha_{off-target}, t_l), \text{ respectively; and}$$

(iii)
   $$D_{target} = C_{target} \text{ and } D_{off-target} = C_{off-target}, \text{ respectively;}$$

wherein $\alpha_{target}$ is a scaling constant of a scaling transformation of said target pathway, $\alpha_{off\text{-}target}$ is a scaling constant of a scaling transformation of said at least one of its off-target pathways, $R_{target, k}(\alpha_{target}, t_l)$ is a scaled response of cellular constituent k in said target pathway and $R_{off\text{-}target, k}(\alpha_{off\text{-}target}, t_l)$ is a scaled response of cellular constituent k in said at least one of its off-target pathways, $t_l$ is a drug exposure level, $\beta_k$ is a constant for cellular constituent k, $C_{target}$ is the minimal level of said drug to achieve a threshold response in said target pathway, and $C_{off\text{-}target}$ is the minimal level of said drug to achieve a threshold response in said at least one of its off-target pathways; thereby evaluating specificity of said drug; and b) displaying or outputting a result of said comparing step a) to a user, a computer readable storage medium, a monitor, or a computer that is part of a network.

2. The method of claim 1 wherein said $D_{target}$ and $D_{off\text{-}target}$ are measured according to a method comprising:
   a) applying a plurality of levels of said drug to said biological sample and measuring a plurality of cellular constituents in said biological sample at each level of said drug to obtain a first profile of graded drug response;
   b) applying said plurality of levels of said drug to a test sample, wherein said test sample is the same as said biological sample except that said target pathway is not functional in said test sample, and measuring said plurality of cellular constituents in said test sample at each level of said drug to obtain a second profile of graded drug response; and
   c) determining said $D_{target}$ and $D_{off\text{-}target}$ by comparing said first and second profiles.

3. The method of claim 2 wherein said biological sample is a yeast cell, and said test sample is a yeast cell in which a critical gene in said target pathway is. deleted.

4. The method of claim 2 wherein said biological sample is a mammalian cell, and said test sample is a mammalian cell in which a critical gene in said target pathway is deleted.

5. The method of claim 2 wherein said biological sample is an animal, and said test sample is a transgenic animal in which a critical gene in said target pathway is made non-functional.

6. The method of claim 2 wherein said plurality of cellular constituents is a plurality of transcripts of a plurality of genes.

7. The method of claim 2 wherein said plurality of cellular constituents is a plurality of proteins.

8. The method of claim 1 wherein said $D_{target}$ and $D_{off\text{-}target}$ are measured according to a method comprising:
   a) perturbing said target pathway and/or said off target pathway in said biological sample to obtain a perturbation profile consisting of measurements of a plurality of cellular constituents;
   b) applying a plurality of levels of said drug to said biological sample to obtain a drug response profile consisting of measurements of said plurality of cellular constituents at each level of said drug; and
   c) determining said $D_{target}$ and $D_{off\text{-}target}$ by comparing said drug response profile and said perturbation profile.

9. The method of claim 8 wherein said plurality of cellular constituents is a plurality of transcripts of a plurality of genes.

10. The method of claim 8 wherein said plurality of cellular constituents is a plurality of proteins.

11. A method for evaluating specificity of a drug comprising:
    a) comparing activity of a drug against its target pathway ($D_{target}$) in a cell and activity of said drug against at least one of its off-target pathways ($D_{off\text{-}target}$) in said cell, wherein said $D_{target}$ and $D_{off-target}$ are each determined based on measurements of a plurality of cellular constituents of said cell, and wherein said comparing step comprises calculating a specificity index (SI) according to the following formula:

$$SI = \frac{n \cdot D_{target}}{\sum D_{off-target}}$$

wherein: n is the number of off-target pathway; and b) displaying or outputting a result of said comparing step a) to a user, a computer readable storage medium, a monitor, or a computer that is part of a network.

12. A method for evaluating specificity of a drug comprising:

a) measuring activity of a drug against its target pathway to obtain a target activity ($D_{target}$);

b) measuring activity of said drug against at least one pathway other than said target pathway to obtain at least one off-target activity ($D_{off-target}$)

c) determining said specificity by comparing said $D_{target}$ and said $D_{off-target}$;

wherein said $D_{target}$ and $D_{off-target}$ are represented by quantities selected from the group consisting of (i)

$D_{target} = R_{target,k}(\alpha_{target}, t_l)$ and $D_{off-target} = R_{off-target,k}(\alpha_{off-target}, t_l)$, respectively;

(ii)

$D_{target} = \sum_k \beta_k R_{target,k}(\alpha_{target}, t_l)$ and $D_{off-target} = \sum_k \beta_k R_{off-target,k}(\alpha_{off-target}, t_l)$, respectively; and (iii)

$D_{target} = C_{target}$ and $D_{off-target} = C_{off-target}$, respectively;

wherein $\alpha_{target}$ is a scaling constant of a scaling transformation of said target pathway, $\alpha_{off-target}$ is a scaling constant of a scaling transformation of said at least one of its off-target pathways, $R_{target,k}(\alpha_{target}, t_l)$ is a scaled response of cellular constituent k in said target pathway and $R_{off-target,k}(\alpha_{off-target}, t_l)$ is a scaled response of cellular constituent k in said at least one of its off-target pathways, $t_l$ is a drug exposure level, $\beta_k$ is a constant for cellular constituent k, $C_{target}$ is the minimal level of said drug to achieve a threshold response in said target pathway and $C_{off-target}$ is the minimal level of said drug to achieve a threshold response in said at least one of its off-target pathways; and d) displaying or outputting a result of said determining step c) to a user, a computer readable storage medium, a monitor, or a computer that is part of a network.

13. The method of claim 12 wherein said $D_{target}$ and $D_{off-target}$ are measured according to a method comprising:

a) applying a plurality of levels of said drug to said biological sample and measuring a plurality of cellular constituents in said biological sample at each level of said drug to obtain a first profile of graded drug response;

b) applying said plurality of levels of said drug to a test sample, wherein said test sample is the same as said biological sample except that said target pathway is not functional in said test sample, and measuring said plurality of cellular constituents in said test sample at each level of said drug to obtain a second profile of graded drug response; and c) determining said $D_{target}$ and $D_{off-target}$ by comparing said first and second profiles.

14. The method of claim 13 wherein said plurality of cellular constituents is a plurality of transcripts of a plurality of genes.

15. The method of claim 13 wherein said plurality of cellular constituents is a plurality of proteins.

16. The method of claim 13 wherein said biological sample is a yeast cell, and said test sample is a yeast cell in which a critical gene in said target pathway is deleted.

17. The method of claim 13 wherein said biological sample is a mammalian cell, and said test sample is a mammalian cell in which a critical gene in said target pathway is deleted.

18. The method of claim 13 wherein said biological sample is an animal, and said test sample is a transgenic animal in which a critical gene in said target pathway is made nonfunctional.

19. The method of claim 12 wherein said $D_{target}$ and $D_{off-target}$ are measured according to a method comprising:

a) perturbing said target pathway and/or said off target pathway in said biological sample to obtain a perturbation profile consisting of measurements of a plurality of cellular constituents;

b) applying a plurality of levels of said drug to said biological sample to obtain a drug response profile consisting of measurements of said plurality of cellular constituents at each level of said drug; and c) determining said $D_{target}$ and $D_{off-target}$ by comparing said drug response profile and said perturbation profile.

20. The method of claim 19 wherein said plurality of cellular constituents is a plurality of transcripts of a plurality of genes.

21. The method of claim 20 wherein said plurality of cellular constituents is a plurality of proteins.

22. The method of claim 1 or 12, wherein said comparing said $D_{target}$ and said $D_{off-target}$ comprises calculating a specificity index (SI) according to the following formula:

$$SI = \frac{n \cdot D_{target}}{\sum D_{off-target}}$$

wherein: n is the number of off-target pathways.

23. A method for evaluating specificity of a drug comprising:

a) determining activity of a drug against its target pathway in a cell to obtain a target activity ($D_{target}$);

b) determining activity of said drug against at least one pathway other than said target pathway in said cell to obtain at least one off-target activity ($D_{off-target}$);

c) determining said specificity by comparing said $D_{target}$ and said $D_{off-target}$;

wherein said $D_{target}$ and $D_{off-target}$ are each determined based on measurements of a plurality of cellular constituents of said cell, and wherein said determining step comprises calculating a specificity index (SI) according to the following formula:

$$SI = \frac{n \cdot D_{target}}{\sum D_{off-target}}$$

wherein: n is the number of off-target pathways; and d) displaying or outputting a result of said determining step c) to a user, a computer readable storage medium, a monitor, or a computer that is part of a network.

24. The method of claim 11 or 23, wherein said measurements of a plurality of cellular constituents are measurements of levels of gene transcripts.

25. The method of claim 11 or 23, wherein said measurements of a plurality of cellular constituents are measurements of levels of proteins.

26. A method for evaluating specificity of a drug, said method comprising:

(a) decomposing a drug response profile into one or a combination of pathway response profiles, wherein said drug response profile comprises measurements of a plurality of cellular constituents in a biological sample in response to said drug over a plurality of levels of drug exposure, and each said pathway response profile comprises measurements of said plurality of cellular constituents at a plurality of levels of perturbation to a biological pathway, said decomposing comprising representing said drug response profile in terms of said one or a combination of pathway response profiles according to equation $$D_k(t_l) \cong \sum_i R_{i,k}(\alpha_i, t_l)$$

wherein $t_l$ is a level of the drug, $\alpha_i$ is a scaling constant of a scaling transformation of pathway i, $D_k(t_l)$ is the measurement of cellular constituent k in said drug response profile at the drug exposure level of $t_l$, $R_{i,k}(\alpha_i, t_l)$ is the measurement of cellular constituent k in pathway i at the drug exposure level of $t_l$; and (b) comparing, among said one or a combination of pathway response profiles, the pathway response profiles for the one or more biological pathways associated with therapeutic effects of the drug with the pathway response profiles for the one or more biological pathways that are associated with one or more non-therapeutic effects of the drug, thereby evaluating specificity of said; and c) displaying or outputting a result of said comparing step b) to a user, a computer readable storage medium, a monitor, or a computer that is part of a network.

27. A method for evaluating specificity of a drug, said method comprising:

a) decomposing a drug response profile into one or a combination of pathway response profiles, wherein said drug response profile comprises measurements of a plurality of cellular constituents in a biological sample in response to said drug over a plurality of levels of drug exposure, and each said pathway response profile comprises measurements of said plurality of cellular constituents at a plurality of levels of perturbation to a biological pathway, and wherein said decomposing comprises transforming said levels of drug exposure into said levels of perturbation by a horizontal scaling transformation;

b) comparing, among said one or a combination of pathway response profiles, the pathway response profiles for the one or more biological pathways associated with therapeutic effects of the drug with the pathway response profiles for the one or more biological pathways that are associated with one or more non-therapeutic effects of the drug, thereby evaluating specificity of said drug; and c) displaying or outputting a result of said comparing step b) to a user, a computer readable storage medium, a monitor, or a computer that is part of a network.

28. The method of claim 27, wherein said horizontal scaling transformation is a linear transformation.

29. The method of claim 27, wherein said decomposing comprises determining said scaling transformation such that said drug response profile is represented by said one or a combination of pathway response profiles.

30. The method of claim 29, wherein said determining is by a method comprising least squares minimizing the residue between said drug response profile and said one or a combination of pathway response profiles.

31. The method of claim 27, wherein values of said measurements of a plurality of cellular constituents have been converted into cellular constituent set values.

32. The method of claim 29 or 30, wherein said comparing comprises comparing activity of said drug on its target pathway ($D_{target}$) and at least one of its off-target pathways ($D_{off-target}$), wherein said $D_{target}$ and said $D_{off-target}$ are calculated according to equations $$D_{target}(t_l) = \sum_k \beta_k R_{target,k}(\alpha_{target}, t_l) \text{ and}$$

$$D_{off-target}(t_l) = \sum_k \beta_k R_{off-target,k}(\alpha_{off-target}, t_l)$$

where $t_l$ is a level of the drug, $\beta_k$ is a constant for cellular constituent k, $\alpha_{target}$ is a scaling constant of said scaling transformation of said target pathway, $\alpha_{off-target}$ is a scaling constant of said scaling transformation of said off-target pathway, and $R_{target,k}(\alpha_{target}, t_l)$ is the response of cellular constituent k in the target pathway at the drug level $t_l$ and $R_{off-target,k}(\alpha_{off-target}, t_l)$ is the response of cellular constituent k in the off-target pathway at the drug level $t_l$.

33. The method of claim 32, wherein said comparing said $D_{target}$ and said $D_{off-target}$ comprises calculating a specificity index (SI) according to the following formula:

$$SI = \frac{n \cdot D_{target}}{\sum D_{off-target}}$$

wherein: n is the number of off-target pathways.

34. A method for evaluating specificity of a drug, said method comprising:

a) decomposing a drug response profile into one or a combination of pathway response profiles, wherein said drug response profile comprises measurements of a plurality of cellular constituents in a biological sample in response to said drug over a plurality of levels of drug dosage, and each said pathway response profile comprises measurements of said plurality of cellular constituents at a plurality of levels of perturbation to a biological pathway, said decomposing comprising representing said drug response profile in terms of said one or a combination of pathway response profiles according to equation $$D_k(t_l) \cong \sum_i R_{i,k}(\alpha_i, t_l)$$

wherein $t_l$ is a level of the drug, $\alpha_i$ is a scaling constant of a scaling transformation of pathway i, $D_k(t_l)$ is the measurement of cellular constituent k in said drug response profile at the drug exposure level of $t_l$, $R_{i,k}(\alpha_i, t_l)$ is the measurement of cellular constituent k in pathway i at the drug exposure level of $t_l$;

b) comparing among said one or a combination of pathway response profiles, the pathway response profiles for the one or more biological pathways associated with therapeutic effects of the drug with the pathway response profiles for the one or more biological pathways that are associated with one or more non-therapeutic effects of the drug, thereby evaluating specificity of said drug; and c) displaying or outputting a result of said comparing step b) to a user, a computer readable storage medium, a monitor, or a computer that is part of a network.

35. The method of claim 26 or 34, wherein said comparing is carried out by a method comprising comparing $$R_{target,k}(\alpha_{target}, t_l) \text{ with } R_{off-target,k}(\alpha_{off-target}, t_l); \text{ or}$$

$$\sum_k \beta_k R_{target,k}(\alpha_{target}, t_l) \text{ with}$$

$$\sum_k \beta_k R_{off-target,k}(\alpha_{off-target}, t_l); \text{ wherein } R_{target,k}(\alpha_{target}, t_l)$$

is a scaled response of cellular constituent k in a pathway associated with therapeutic effects of the drug, $R_{off-target, k}(\alpha_{off-target}, t_l)$ is a scaled response of cellular constituent k in a pathway associated with one or more non-therapeutic effects of the drug, and $\beta_k$ is a constant for cellular constituent k.

* * * * *